US006875348B2

(12) United States Patent
Zare et al.

(10) Patent No.: US 6,875,348 B2
(45) Date of Patent: Apr. 5, 2005

(54) SEPARATION COLUMN HAVING A PHOTOPOLYMERIZED SOL-GEL COMPONENT AND ASSOCIATED METHODS

(75) Inventors: Richard N. Zare, Stanford, CA (US); Maria T. Dulay, Sunnyvale, CA (US); Joselito P. Quirino, Sunnyvale, CA (US); Bryson D. Bennett, Murray, UT (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 10/124,654

(22) Filed: Apr. 16, 2002

(65) Prior Publication Data

US 2003/0062310 A1 Apr. 3, 2003

Related U.S. Application Data

(63) Continuation-in-part of application No. 10/008,482, filed on Nov. 13, 2001, now abandoned, which is a continuation-in-part of application No. 09/507,707, filed on Feb. 18, 2000, now abandoned, and a continuation-in-part of application No. 09/929,275, filed on Aug. 13, 2001.

(51) Int. Cl.⁷ .............................................. B01D 15/08
(52) U.S. Cl. ............................... 210/198.2; 210/198.3; 210/635; 210/656; 210/658
(58) Field of Search .................... 210/635, 656, 210/659, 198.2, 658, 198.3; 95/82, 88; 96/101

(56) References Cited

U.S. PATENT DOCUMENTS

| 3,503,712 A | 3/1970 | Sussman ................ 219/198.2 |
| 3,568,840 A | 3/1971 | Hashimoto et al. ...... 210/198.2 |
| 3,757,490 A | 9/1973 | Ma ........................... 210/198.2 |

(Continued)

FOREIGN PATENT DOCUMENTS

| EP | 0 439 318 A2 | 7/1991 | ............... 210/198.2 |
| EP | 0 779 512 B1 | 6/1997 | ............... 210/198.2 |
| WO | WO 99/30147 | 6/1999 | ............... 210/198.2 |
| WO | WO 00/49396 | 8/2000 | ............... 210/198.2 |

OTHER PUBLICATIONS

Hawley, the Condensed Chemical Dictionary, Van Nostrand, New York, 1971 p. 558.*

Chong et al., "Sol–Gel Coating Technology for the Preparation of Solid–Phase Microextraction Fibers of Enhanced Thermal Stability," *Analytical Chemistry*, vol. 69, No. 19, Oct. 1, 1997, pp. 3889–3898.

Righetti et al., "'Laterally Aggregated' Polyacrylamide Gels for Electrophoresis," *Electrophoresis*, 13, 1992, pp. 587–595.

(Continued)

*Primary Examiner*—Ernest G. Therkorn
(74) *Attorney, Agent, or Firm*—Parsons Hsue & de Runtz LLP

(57) ABSTRACT

A separation column and a method of preparing the separation column are provided. The separation column includes a separation channel and a porous matrix in the channel. The porous matrix includes a metal organic polymer, such as a photopolymer. The porous matrix can be a separation medium adapted to separate a sample of analytes or a frit adapted to retain a separation medium in the channel.

17 Claims, 20 Drawing Sheets

U.S. PATENT DOCUMENTS

| | | | | |
|---|---|---|---|---|
| 3,808,125 | A | | 4/1974 | Good .................... 210/198.2 |
| 3,878,092 | A | | 4/1975 | Fuller .................... 210/198.2 |
| 4,293,415 | A | | 10/1981 | Bente, III et al. ....... 210/198.2 |
| 4,323,439 | A | | 4/1982 | O'Farrell ............... 204/180 G |
| 4,617,102 | A | | 10/1986 | Tomblin et al. ........ 204/299 R |
| 4,675,300 | A | | 6/1987 | Zare et al. ................ 436/172 |
| 4,790,919 | A | | 12/1988 | Baylor, Jr. .............. 204/182.8 |
| 4,793,920 | A | * | 12/1988 | Cortes .................... 210/198.2 |
| 5,085,756 | A | | 2/1992 | Swedberg ............... 204/299 R |
| 5,116,471 | A | | 5/1992 | Chien et al. ............ 204/180.1 |
| 5,116,495 | A | | 5/1992 | Prohaska ................. 219/198.2 |
| 5,135,627 | A | | 8/1992 | Soane .................... 210/198.2 |
| 5,200,150 | A | * | 4/1993 | Rose, Jr. .................... 422/62 |
| 5,202,010 | A | | 4/1993 | Guzman ................ 204/299 R |
| 5,308,495 | A | | 5/1994 | Avnir et al. ............ 210/198.2 |
| 5,316,680 | A | | 5/1994 | Frechet et al. .......... 210/198.2 |
| 5,334,310 | A | | 8/1994 | Frechet et al. .......... 210/198.2 |
| 5,340,452 | A | | 8/1994 | Brenner et al. ......... 204/180.1 |
| 5,423,966 | A | | 6/1995 | Wiktorowicz ........... 204/182.8 |
| 5,453,185 | A | | 9/1995 | Frechet et al. .......... 210/198.2 |
| 5,453,382 | A | | 9/1995 | Novotny et al. ............ 436/178 |
| 5,552,994 | A | | 9/1996 | Cannon et al. ......... 210/198.2 |
| 5,599,445 | A | | 2/1997 | Betz et al. ............... 210/198.2 |
| 5,624,875 | A | * | 4/1997 | Nakanishi et al. ............ 501/39 |
| 5,637,135 | A | | 6/1997 | Ottenstein et al. ............ 96/101 |
| 5,647,979 | A | | 7/1997 | Liao et al. ............... 210/198.2 |
| 5,667,674 | A | | 9/1997 | Hanggi et al. ........... 210/198.2 |
| 5,719,322 | A | | 2/1998 | Lansbarkis et al. ...... 210/198.2 |
| 5,728,296 | A | | 3/1998 | Hjerten et al. .......... 210/198.2 |
| 5,728,457 | A | | 3/1998 | Frechet et al. .......... 210/198.2 |
| 5,759,405 | A | | 6/1998 | Anderson, Jr. et al. ..... 210/656 |
| 5,766,435 | A | | 6/1998 | Liao et al. .................. 204/451 |
| 5,772,875 | A | | 6/1998 | Pettersson et al. ....... 210/198.2 |
| 5,800,692 | A | | 9/1998 | Naylor et al. ............... 204/601 |
| 5,858,241 | A | | 1/1999 | Dittmann et al. .......... 210/656 |
| 5,916,427 | A | | 6/1999 | Kirkpatrick ................ 204/469 |
| 5,938,919 | A | | 8/1999 | Najafabadi ............... 210/198.2 |
| 6,136,187 | A | | 10/2000 | Zare et al. ............... 210/198.2 |
| 6,210,570 | B1 | * | 4/2001 | Holloway ............... 210/198.2 |
| 6,398,962 | B1 | * | 6/2002 | Cabrera .................... 210/198.2 |
| 6,402,918 | B1 | * | 6/2002 | Schlenoff .................... 204/601 |
| 6,531,060 | B1 | * | 3/2003 | Nakanishi ................ 210/198.2 |
| 6,562,744 | B1 | * | 5/2003 | Nakanishi ................ 210/198.2 |

OTHER PUBLICATIONS

Righetti et al., "On the Limiting Pore Size of Hydrophilic gels for Electrophoresis and Isoeletric Focusing," *Journal of Biochemical and Biophysical Methods*; 4, 1981, pp. 347–363.

Guo et al., "Modification of the Inner Capillary Surface by the Sol–Gel Method: Application to Open Tubular Electrochromatography," *J. Microcolumn Separations*, vol. 7, No. 5, 1995, pp. 485–491.

Tsuda et al., "Rectangular Capillaries for Capillary Zone Electrophoresis," *Analytical Chemistry*, vol. 62, No. 19, Oct. 1, 1990, pp. 2149–2152.

Swartz et al., "On–line Sample Preconcentration on a Packed–Inlet Capillary for Improving the Sensitivity of Capillary Electrophoretic Analysis of Pharmaceuticals," *Journal of Chromatography*, 632, 1993, pp. 209–213.

Guo et al., "Hydrolytically Stable Amino–Silica Glass Coating Material for Manipulation of the Electroosmotic Flow in Capillary Electrophoresis," *Journal of Chromatography A*, 744, 1996, pp. 17–29.

Burgi et al., "Optimization in Sample Stacking for High–Performance Capillary Electrophoresis," *Analytical Chemistry*, vol. 63, No. 18, Sep. 15, 1991, pp. 2042–2047.

Etienne et al., "Photocurable Sol–Gel Coatings: Channel Waveguides for use at 1.5 μm," *Journal of Sol–Gel Science and Technology*, 13, 1998, pp. 523–527.

Kenny et al., "Micropreparative Capillary Electrophoresis (MPCE) and Micropreparative HPLC of Protein Digests," *Techniques in Protein Chemistry III*, 1993, pp. 363–370.

Smith et al., "Micropreparative Separation of Typtic Digests by Capillary Electrophoresis and Characterization by Protein Sequencing," *Techniques in Protein Sequencing III*, 1992, pp. 113–120.

Horak et al., "The Effect of Polymeric Porogen on the Properties of Macroporous Poly(glycidyl) Methacrylate–*co*– ethylene Dimethacrylate)," *Polymer*, vol. 34, No. 16, 1993, pp. 3481–3489.

International Search Report mailed Oct. 25, 2002.

Boughtflower et al., "Capillary Electrochromatography—Some Important Considerations in the Preparation of Packed Capillaries and the Choice of Mobile Phase Buffers," *Chromatographia*, vol. 40, No. 5/6, Mar. 1995, pp. 329–335.

Copy of International Search Report mailed Jan. 3, 2003.

C. Yu et al., "Towards Stationary Phases for Chromatography on a Microchip: Molded Porous Polymer Monoliths Prepared in Capillaries by Photointiated In Situ Polymerization as Separation Media for Electrochromatography," *Electrophoresis* vol. 21, 2000, pp. 120–127.

J. Quirino et al., "Sweeping of Analyte Zones in Electrokinetic Chromatography," *Analytical Chemistry*, vol. 71, No. 8, Apr. 15, 1999, pp. 1638–1644.

M. Taylor et al., "Analysis of Corticosteroids in Biofluids by Capillary Electrochromatography with Gradient Elution," *Analytical Chemistry*, vol. 69, No. 13, Jul. 1, 1997. pp. 2554–2558.

D.A. Stead et al., "Capillary Electrochromatography of Steroids Increased Sensitivity by On–Line Concentration and Comparison with High–Performance Liquid Chromatography," *Journal of Chromatography A*. vol. 798, 1998, pp. 259–267.

Y. Zhang et al., "High–Efficiency On–Line Concentration Technique of Capillary Electrochromatography," *Analytical Chemistry*, vol. 72, No. 22, Nov. 15, 2000, pp. 5744–5747.

T. Tegeler et al., "On–Column Trace Enrichment by Sequential Frontal and Elution Electrochromatography. 1. Application to Carbamate Insecticides," *Analytical Chemistry*, vol. 73, No. 14, Jul. 15, 2001, pp. 3365–3372.

F. E. P. Mikkers et al., "Concentration Distributions in Free Zone Electrophoresis," *Journal of Chromatography*, vol. 169, Feb. 1, 1979, pp. 1–10.

R.–L. Chien et al., "On–Column Sample Concentration Using Field Amplification in CZE," *Analytical Chemistry*, vol. 64, No. 8, Apr. 15, 1992, pp. 489–496A.

J. Quirino et al., "Exceeding 5000–Fold Concentration of Dilute Analytes in Micellar Electrokinetic Chromatography," *Science*, vol. 282, Oct. 16, 1998, pp. 465–468.

C. Yang et al., "Electrically Driven Microseparation Methods for Pesticides and Metabolites. II: On–line and Off–line Preconcentration of Urea Herbicides in Capillary Electrochromatography," *Electrophoresis*, vol. 20, 1999, pp. 2337–2342.

M. Dulay et al., "Preparation and Characterization of Monolithic Porous Capillary Columns Loaded with Chromatographic Particles," *Analytical Chemistry*, vol. 70, No. 23, Dec. 1, 1998, pp. 5103–5107.

M. Dulay et al., "Photopolymerzed Sol–Gel Monoliths for Capillary Electrochromatography," *Analytical Chemistry*, vol. 73, No. 16, Aug. 15, 2001, pp. 3921–3926.

J. Quirino et al., "New Strategy for On–Line Preconcentration in Chromatographic Separations," manuscript, undate.

J. Quirino et al., "On–Line Preconcentration in Capillary Electrochromatography Using a Porous Monolith, Solvent Gradient and Sample Stacking," manuscript, undated.

M. Kato et al, "Photopolymerized Sol–Gel Frits for Packed Columns in Capillary Electrochromatography," *Journal of Chromatography A*, vol. 924, 2001, pp. 187–195.

J.–R. Chen et a., "Marcoporous Photopolymer Frits for Capillary Electrochromatography," *Analytical Chemistry*, vol. 72, No. 6, Mar. 15, 2000, pp. 1224–1227.

C. Viklund et al., "Molded Macroporous Poly(Glycidyl Methacrylate–Co–Trimethylolpropane Trimethacrylate) Materials with Fine Controlled Porous Properties: Preparation of Monoliths Using Photoinitiated Polymerization," *Chem. Mater.*, vol. 9, No. 2, 1997, pp. 463–471.

M. Dulay et al., "Bonded–Phase Photopolymerized Sol–Gel Monoliths for Reversed Phase Capillary Electrochromatography," *J. Sep. Sci.*, vol. 25, 2002, pp. 3–9.

M. Kato et al., "Effect of Preparatory Conditions on the Performance of Photopolymerized Sol–Gel Monoliths for Capillary Electrochromatography," *Journal of Chromatography A*, vol. 961, 2002, pp. 45–51.

M. Kato et al., "Enantiomeric Separation of Amino Acids and Nonprotein Amino Acids a Particle–Loaded Monolithic Column," *Electrophoresis*, vol. 21, 2000, pp. 3145–3151.

J. Quirino et al., "On–Line Preconcentration in Capillary Electrochromatography Using a Porous Monolith Together with Solvent Gradient and Sample Stacking," *Anal. Chem.*, vol. 73, 2001, pp. 5557–5563.

J. Quirino et al., "Strategy for On–Line Preconcentration in Chromatographic Separations," *Anal. Chem.*, vol. 73, 2001, pp. 5539–5543.

K. Morishima et al., "Toward Sol–Gel Electrochromatographic Separations on a Chip," *J. Sep. Sci.*, vol. 25, 2002, pp. 1226–1230.

M.J. Hilhorst et al., "Sensitivity Enhancement in Capillary Eletrochromatography by On–Column Preconcentration," *Chromatographia 2001*, 53, Feb. (No. 3/4), pp. 190–196.

Woo, et al., "Photopolymerization of Methyl Methacrylate with Primary and Aryl– and Aiklylsilanes," *Bulletin of the Korean Chemical Society*, vol. 16, No. 11, ISSN 0253–2964, No. 20, 1995.

Cikalo, et al., "Capillary Electrochromatography," *Analyst*, Jul. 1998, vol. 123 pp. 87R–102R.

Quirino, et al., "Sample Stacking of Cationic and Anionic Analytes in Capillary Electrophoresis," *Journal of Chromatography*, A, 902 2000, pp. 119–135.

Quirino, et al. "Sweeping of Neutral Analytes in Electrokinetic Chromatography with High–Salt–Containing Matrixes," *Analytical Chemistry*, vol. 72, No. 8, Apr. 15, 2000.

Chen, et al., "Semipreparative Capillary Electrochromatography." *Analytical Chemistry*, vol. 73, No. 9, May 1, 2001.

Colon et al., "Packing Columns for Capillary Electrochromatography," *Journal of Chromatography*, A. 887 (2000) pp. 43–53.

Svec, et al., "Design of the Monolithic Polymers used in Capillary Electrochromatography Columns," *Journal of Chromatography*, A, 887 (2000) pp. 3–29.

Constantin, et al., "Preparation of Stationary Phasese for Open–Tubular Capillary Electrochromatography Using the Sol–Gel Method," *Journal of Chromatography*, A, 887 (2000) pp. 253–263.

Tan, et al., "Preparation and Evaluation of Bonded Linear Polymethacrylate Stationary Phases for Open Tubular Capillary Electrokinetic Chromatography," *Analytical Chemistry*, vol. 69, No. 4, Feb. 15, 1997.

Chirica, et al., "Fritless Capillary Columns for HPLC and CEC Prepared by Immobilizing the Stationary Phase in an Organic Polymer Matrix," *Analytical Chemistry*, vol. 72, No. 15, Aug. 1, 2000, pp. 3605–3610.

Palm, et al., Macroporous Polyacrylamide/Poly(ethylene glycol) Matrixes as Stationary Phases in Capillary Electrochromatography, *Analytical Chemistry*, vol. 69, No. 22, Nov. 15, 1997, pp. 4499–4507.

Hayes, et al., "Sol–Gel Monolithic Columns with Reversed Electrochromotic Flow for Capillary Electrochromatography," *Analytical Chemistry*, vol. 72, No. 17, Sep. 1, 2000, pp. 4090–4099.

Mol, et al., "Trace Level Analysis of Micropollutants in Aqueous Samples using Gas Chromatography with On–Line Sample Enrichment and Large Volume Injection," *Journal of Chromatography A*, 703 (1995) pp. 277–307.

Quirino, et al., "Approaching a Million–Fold Sensitivity Increase in Capillary Electrophoresis with Direct Ultraviolet Detection: Cation–Selective Exhaustive Injection and Sweeping," *Analytical Chemistry*, vol. 72, No. 5, Mar. 1, 2000, pp. 1023–1030.

Rudge, et al., "Solute Retention in Electrochromatography by Electrically Induced Sorption," *AIChE Journal*, May 1993, vol. 39, No. 5, pp. 797–808.

Kitagawa, et al., "Voltage–Induced Sample Release from Anion Exchange Supports in Capillary Electrochromatography," *Analytical Sciences*, Jun. 1998, vol. 14, pp. 571–575.

Josic, et al., "Monoliths as Stationary Phases for Separation of Proteins and Polynucleotides and Enzymatic Conversion," *Journal of Chromatography B*, 752 (2001) pp. 191–205.

Peters, et al., "Molded Rigid Polymer Monoliths as Separation Media for Capillary Electrochromatography," *Analytical Chemistry*, vol. 69, No. 17, Sep. 1, 1997.

Dulay, et al., "Automated Capillary Alectrochromatography: Reliablility and Reproducibility Studies," *Journal of Chromatography A*, 725 (1996) pp. 361–366.

Brinker, et al., "Sol–Gel Science: The physics and Chemistry of Sol–Gel Processing," *Academic Press*, San Diego, pp. 372–385, 408–411, 458–459 1990.

Badini et al., "Impregnation of a pH–Sensitive Dye into Sol–Gels for Fibre Optic Chemical Sensors," *Analyst, 120*, pp. 1025–1028, Apr. 1995.

Snyder, Introduction to Modern Liquid Chromatography, *John Wiley & Sons, Inc.*, New York, 1979, pp. 145–147.

\* cited by examiner

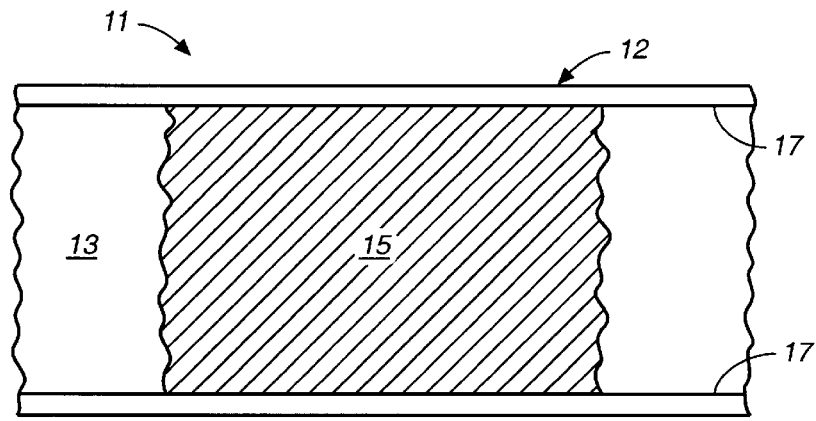
FIG._1A
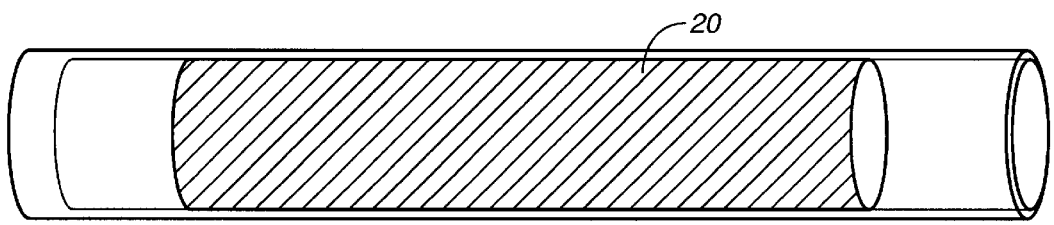
FIG._1B
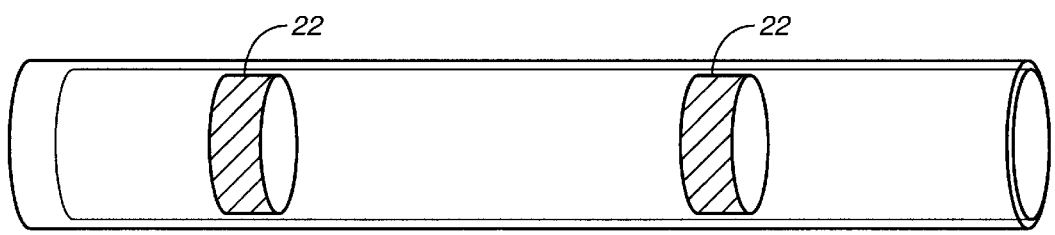
FIG._1C

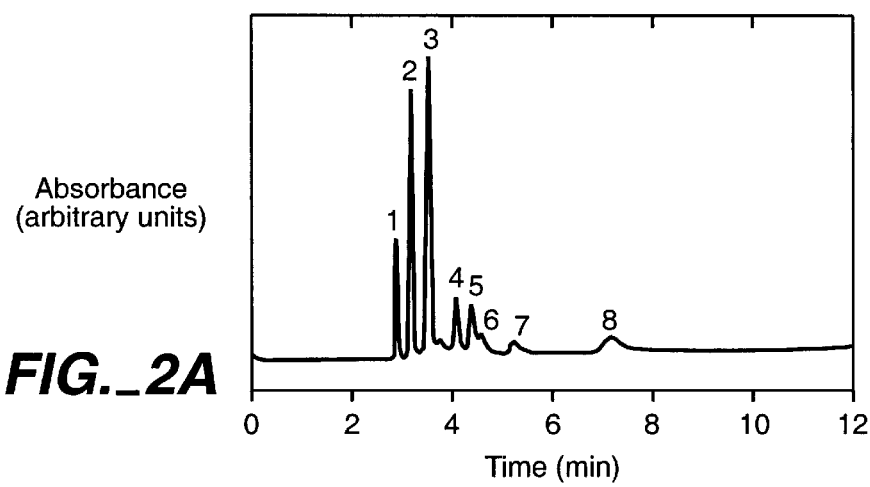
FIG._2A
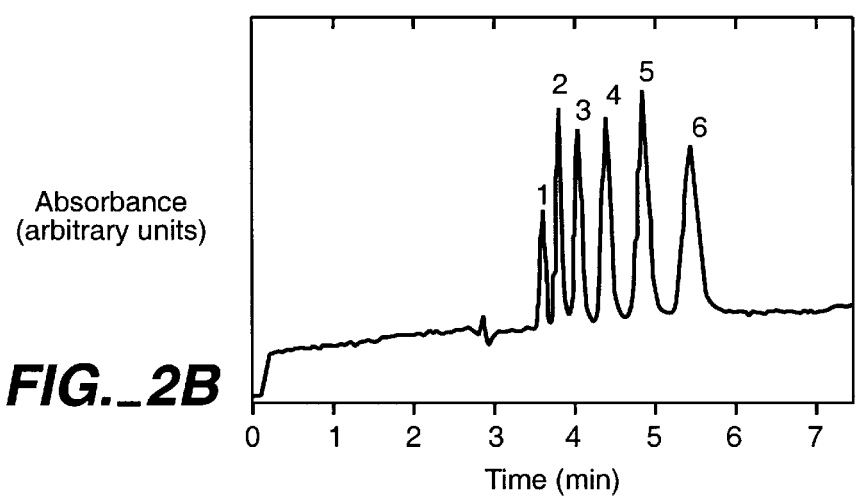
FIG._2B
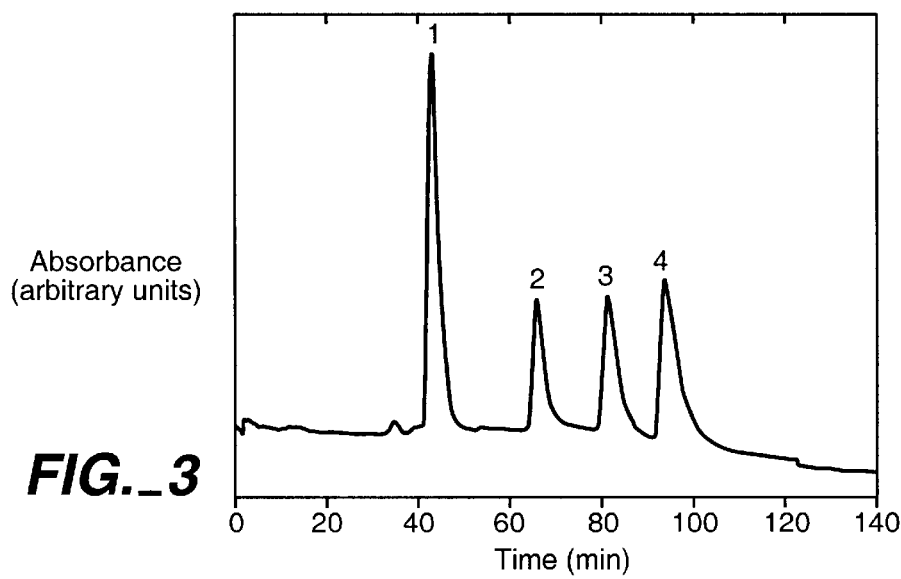
FIG._3

FIG._4A
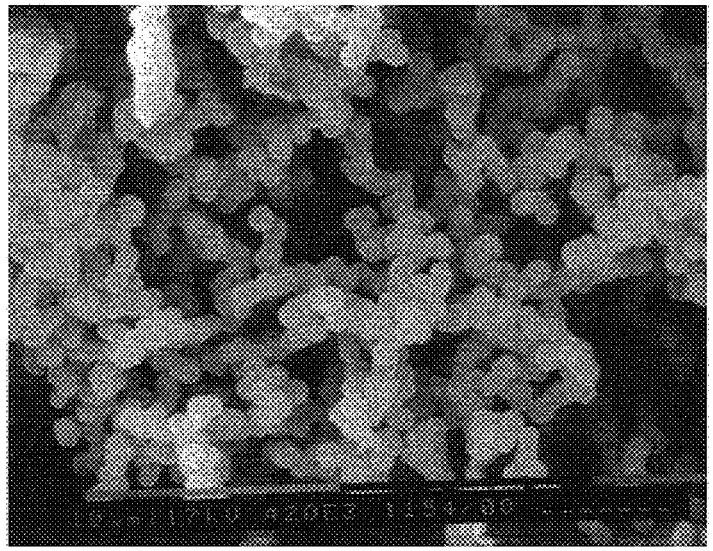
FIG._4B
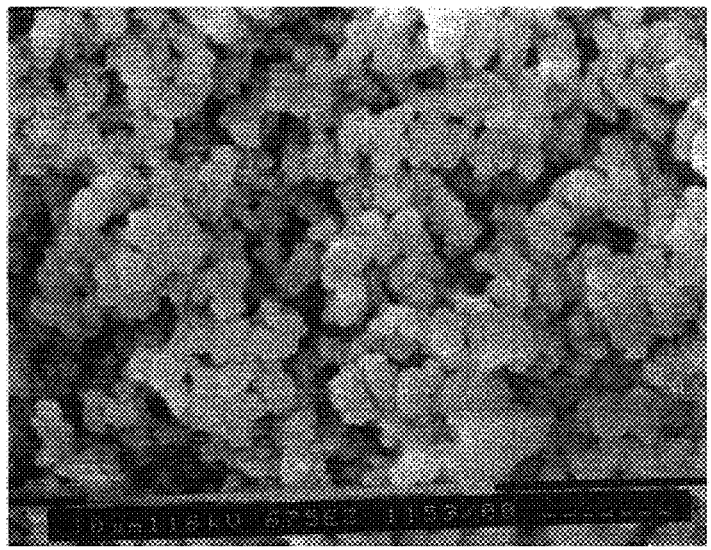

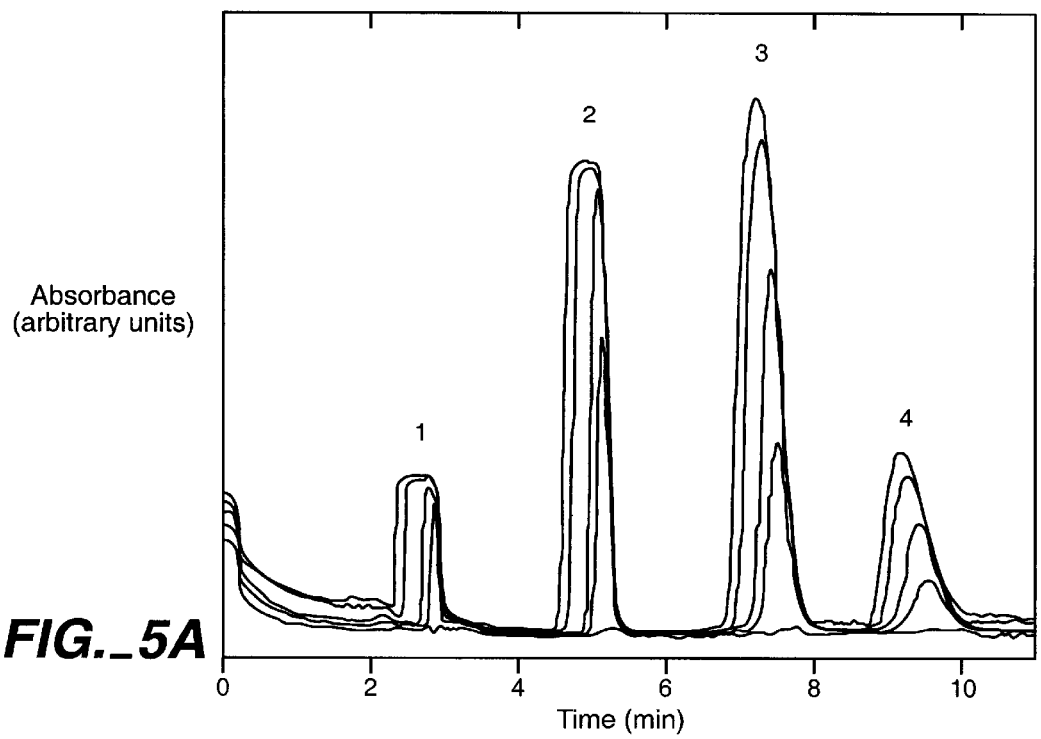
FIG._5A
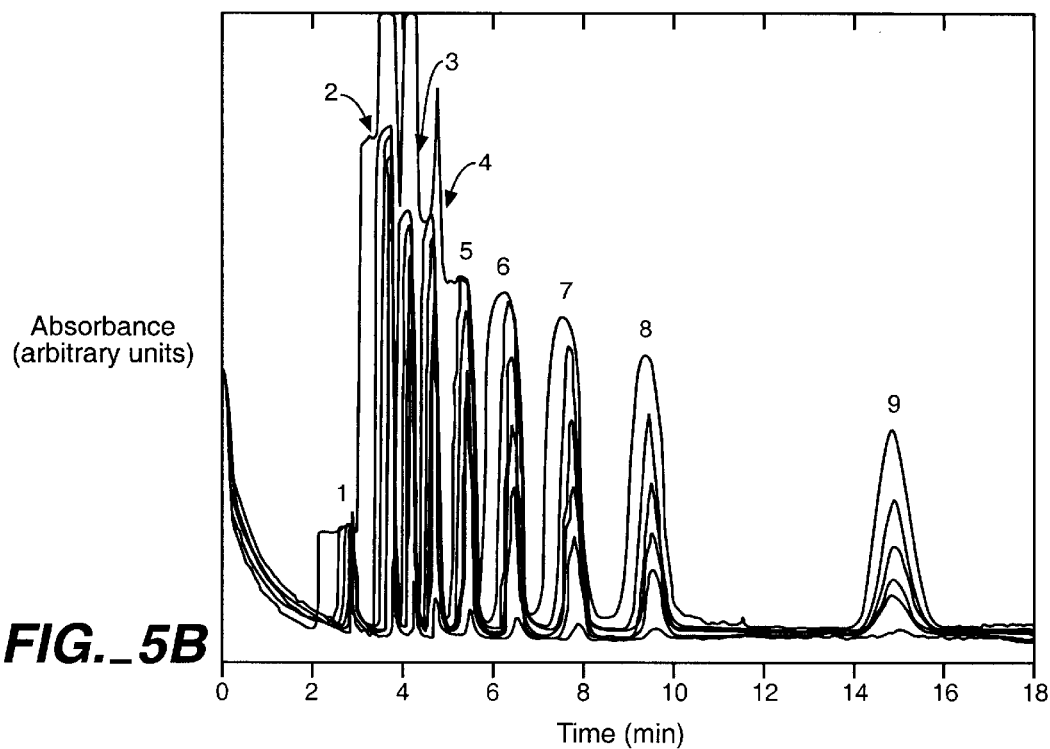
FIG._5B

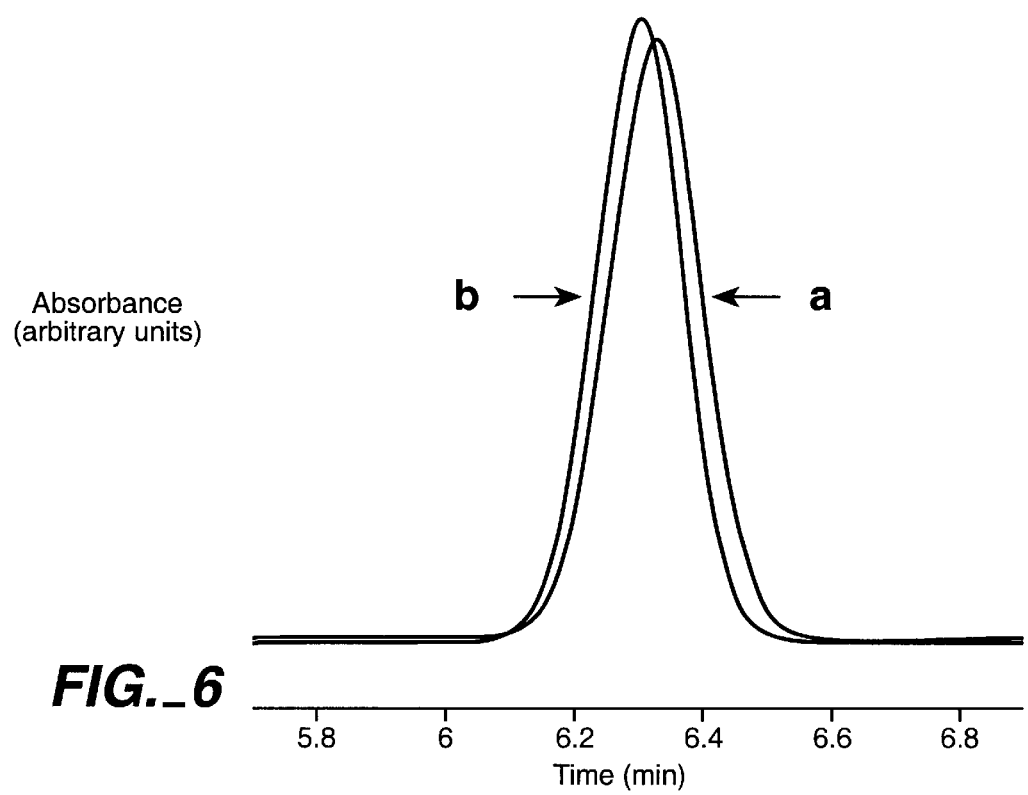
FIG._6
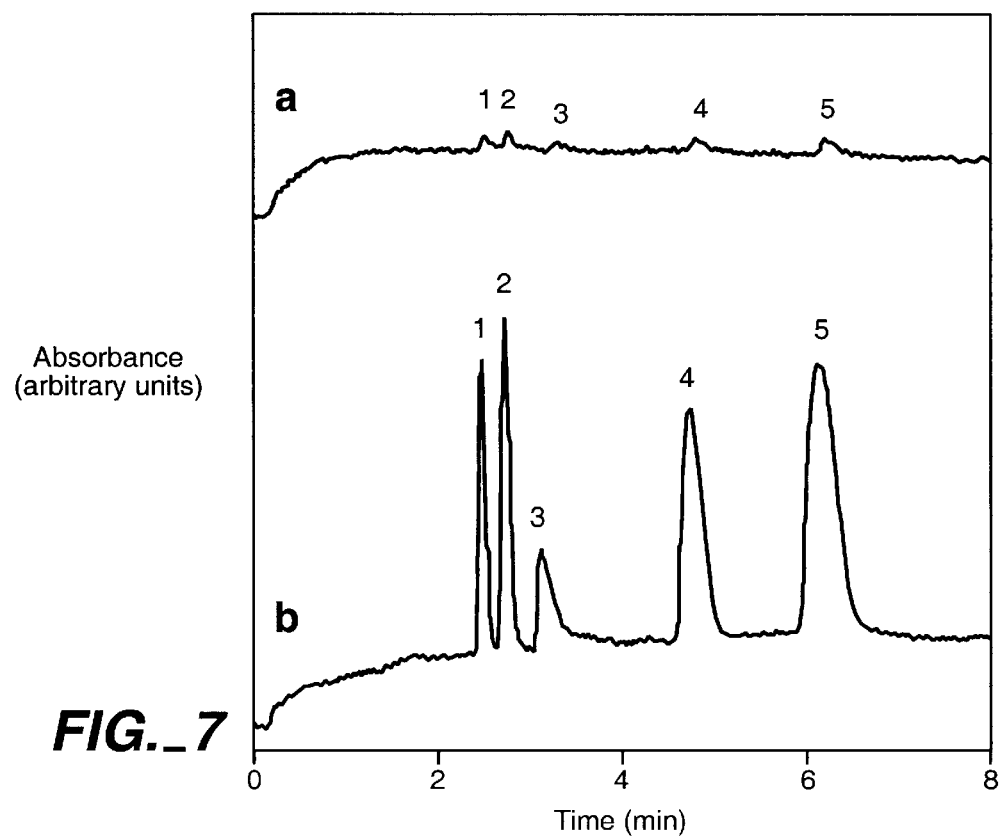
FIG._7

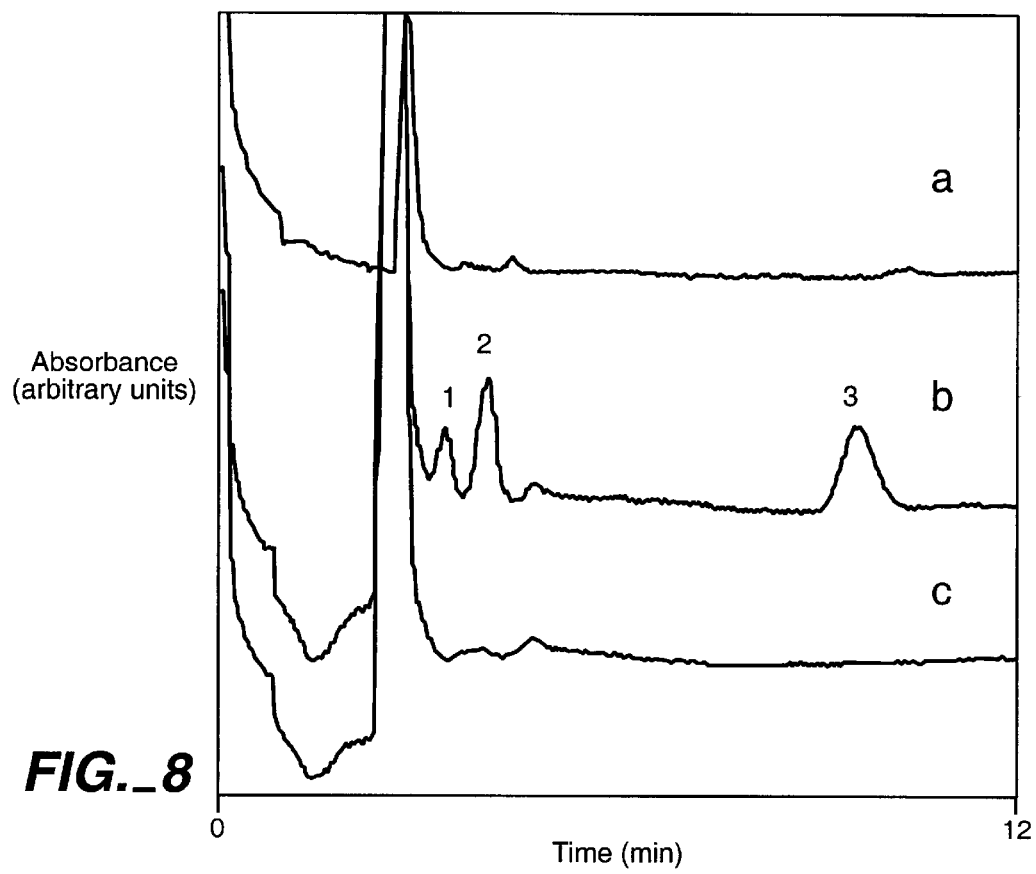
FIG._8

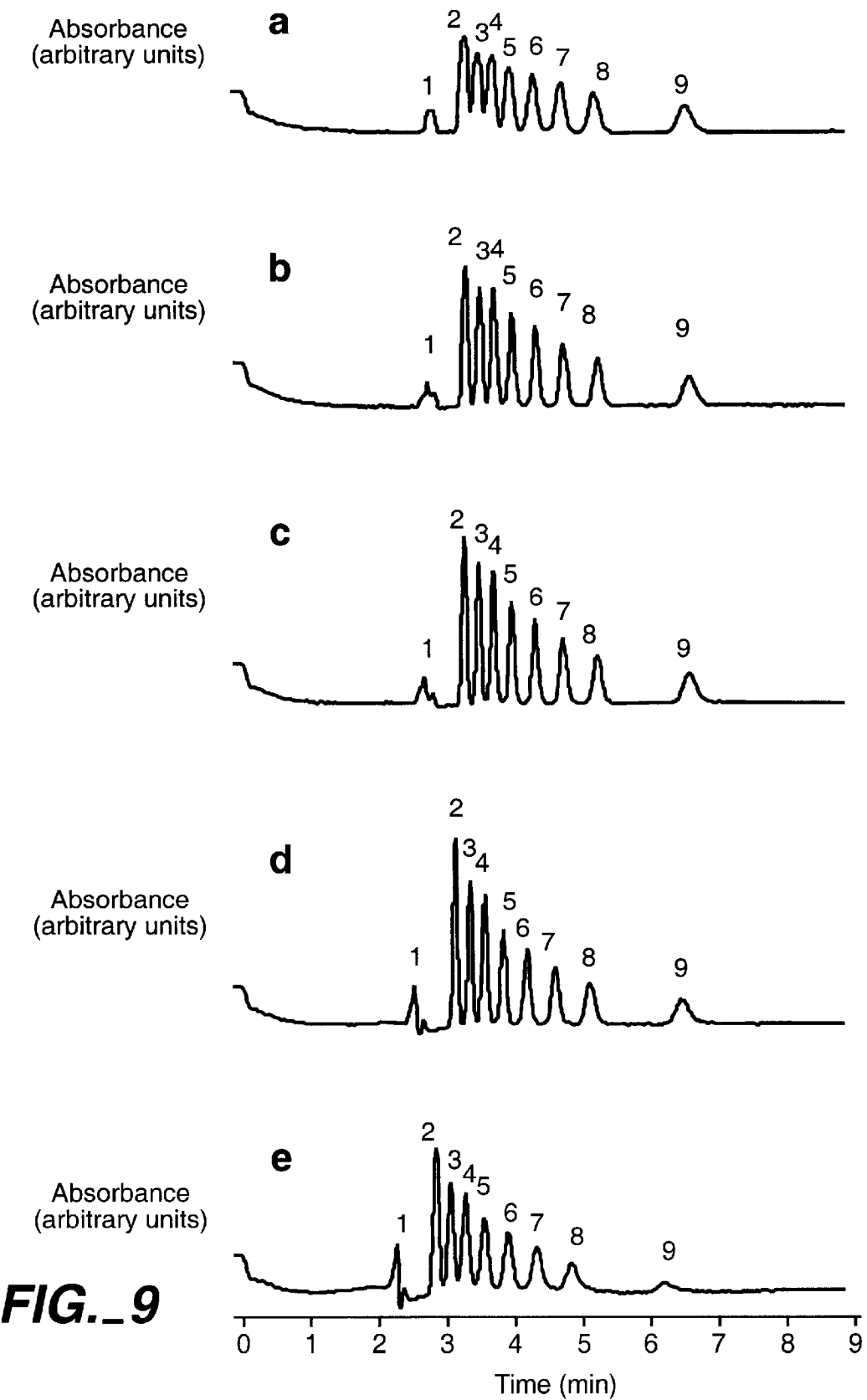
FIG._9

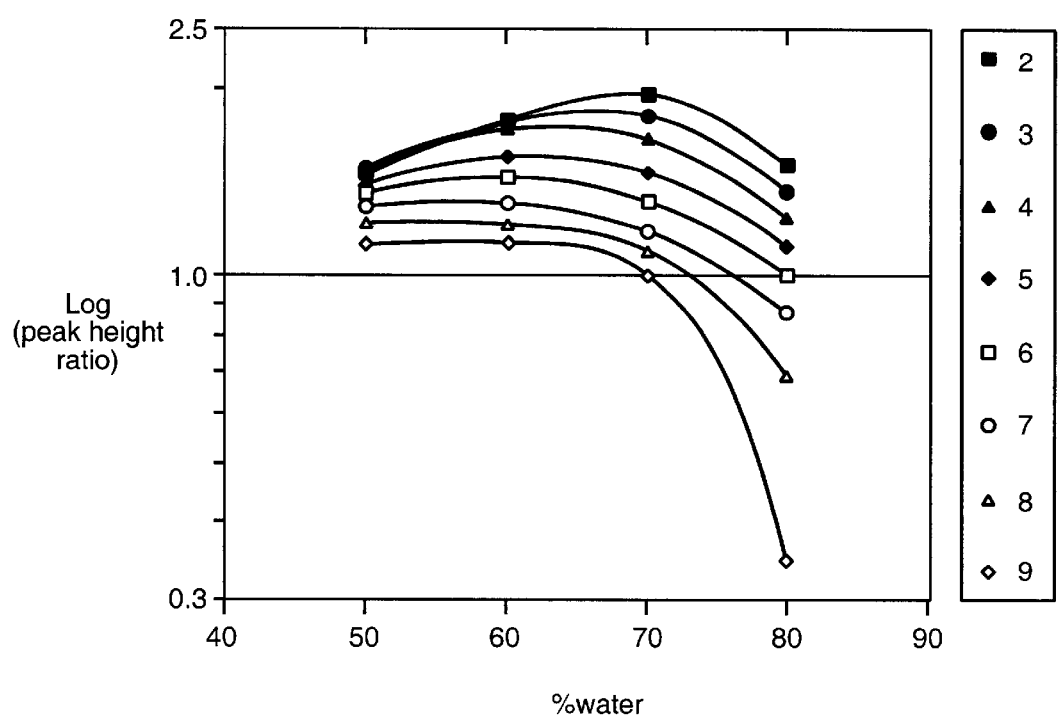
FIG._10

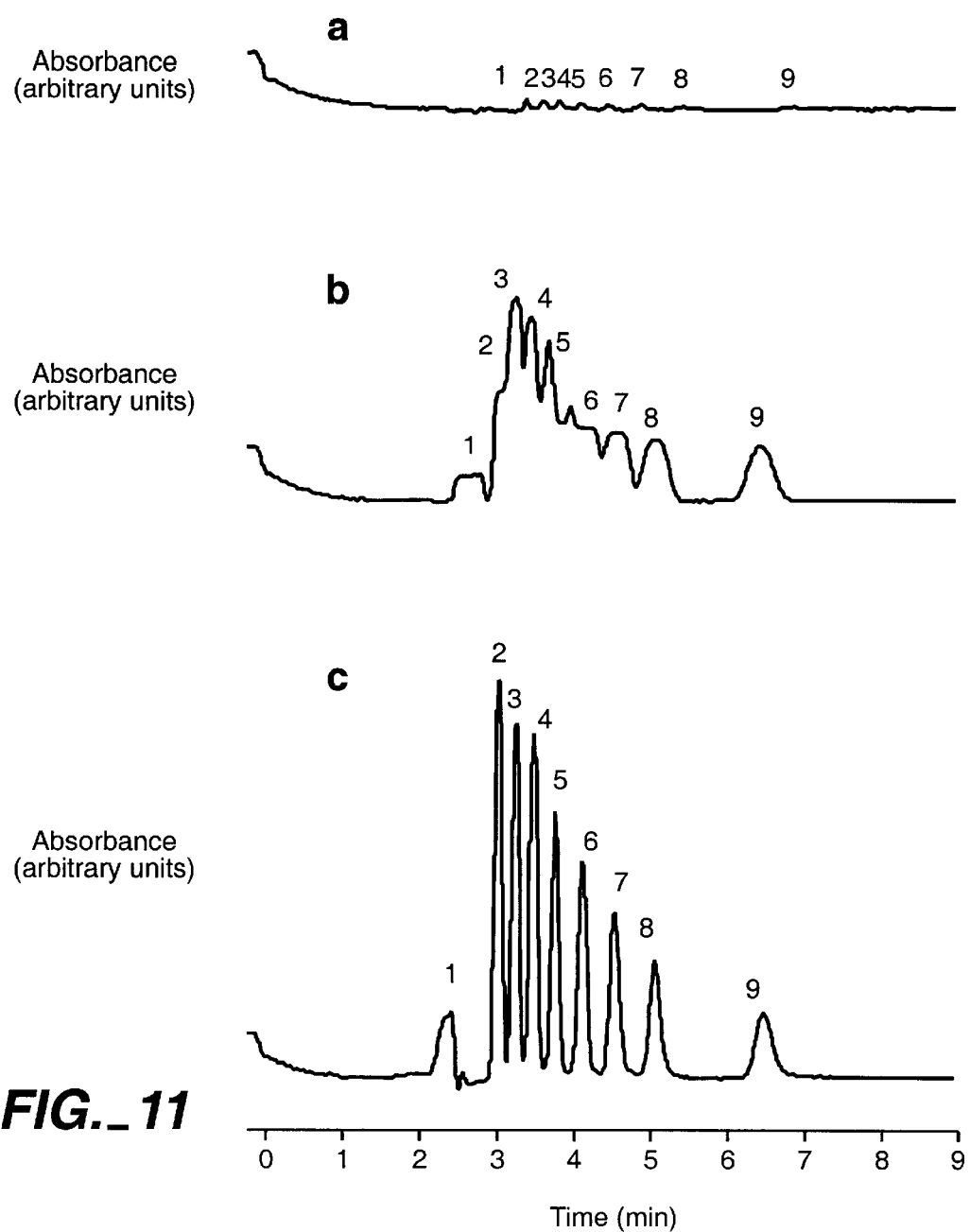
FIG._11

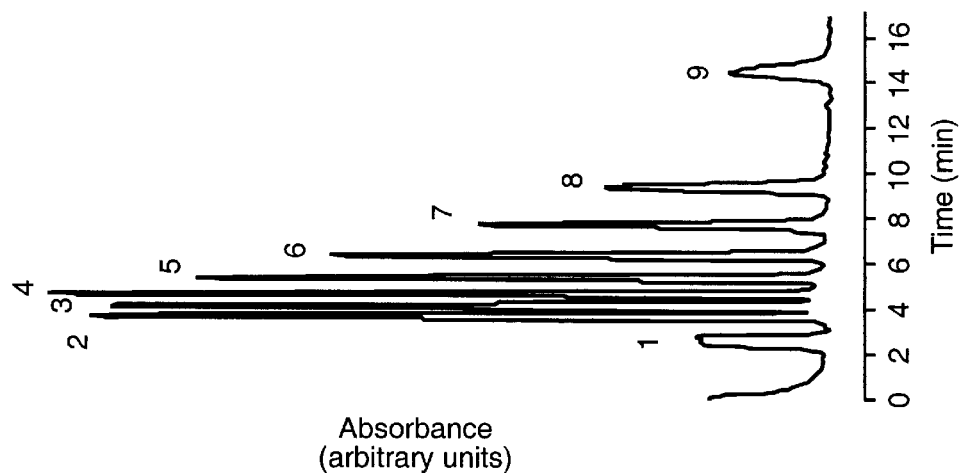
FIG._12C
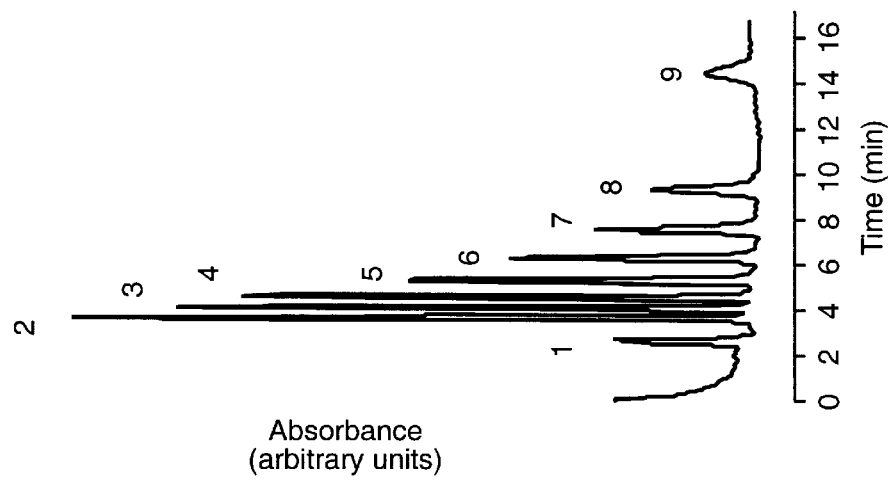
FIG._12B
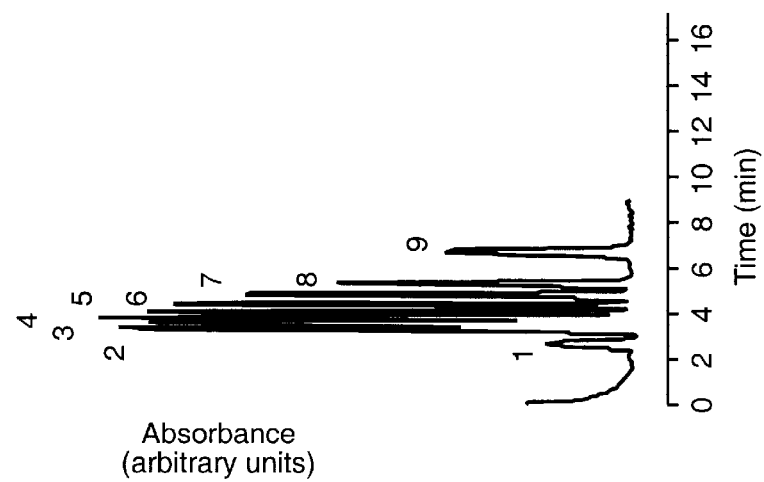
FIG._12A

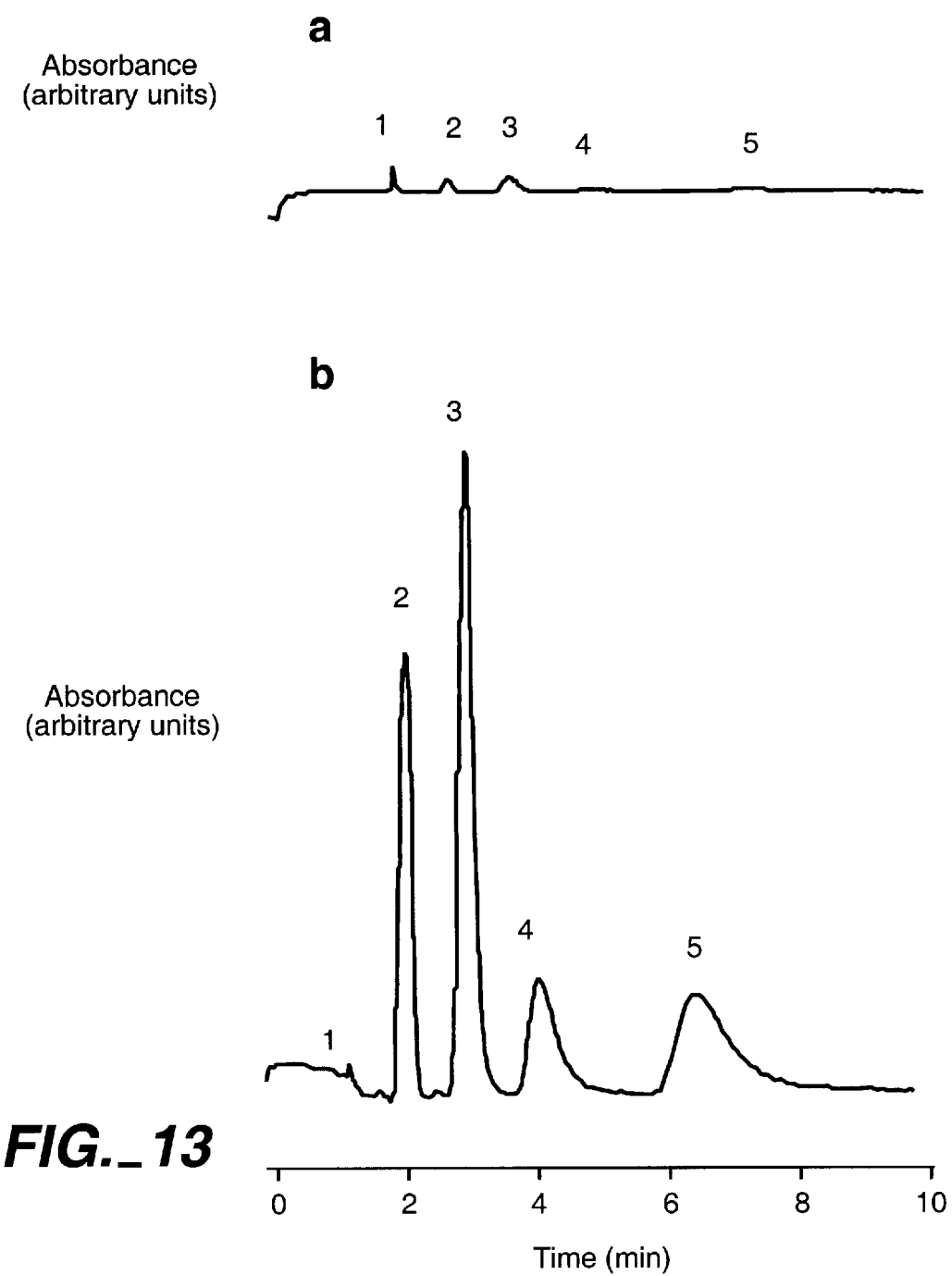
FIG._13

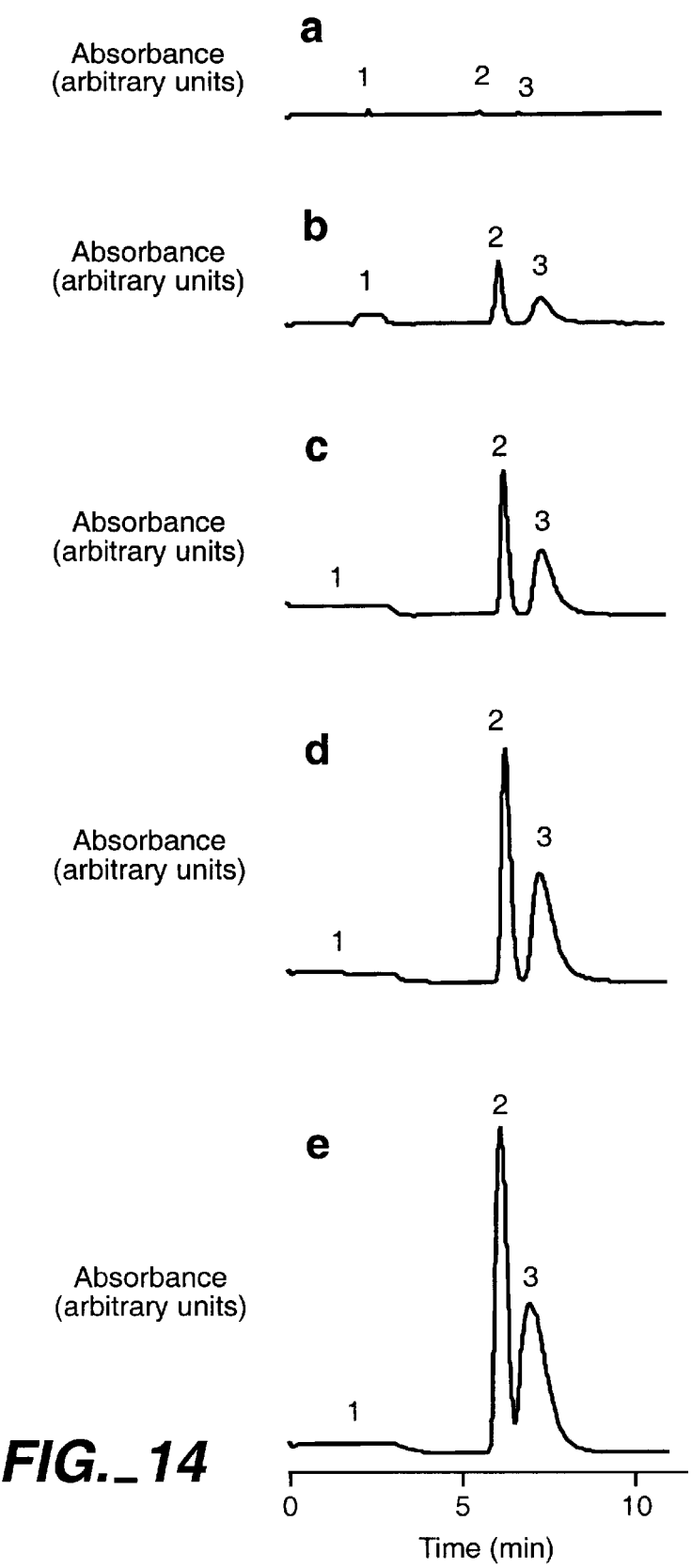
FIG._14

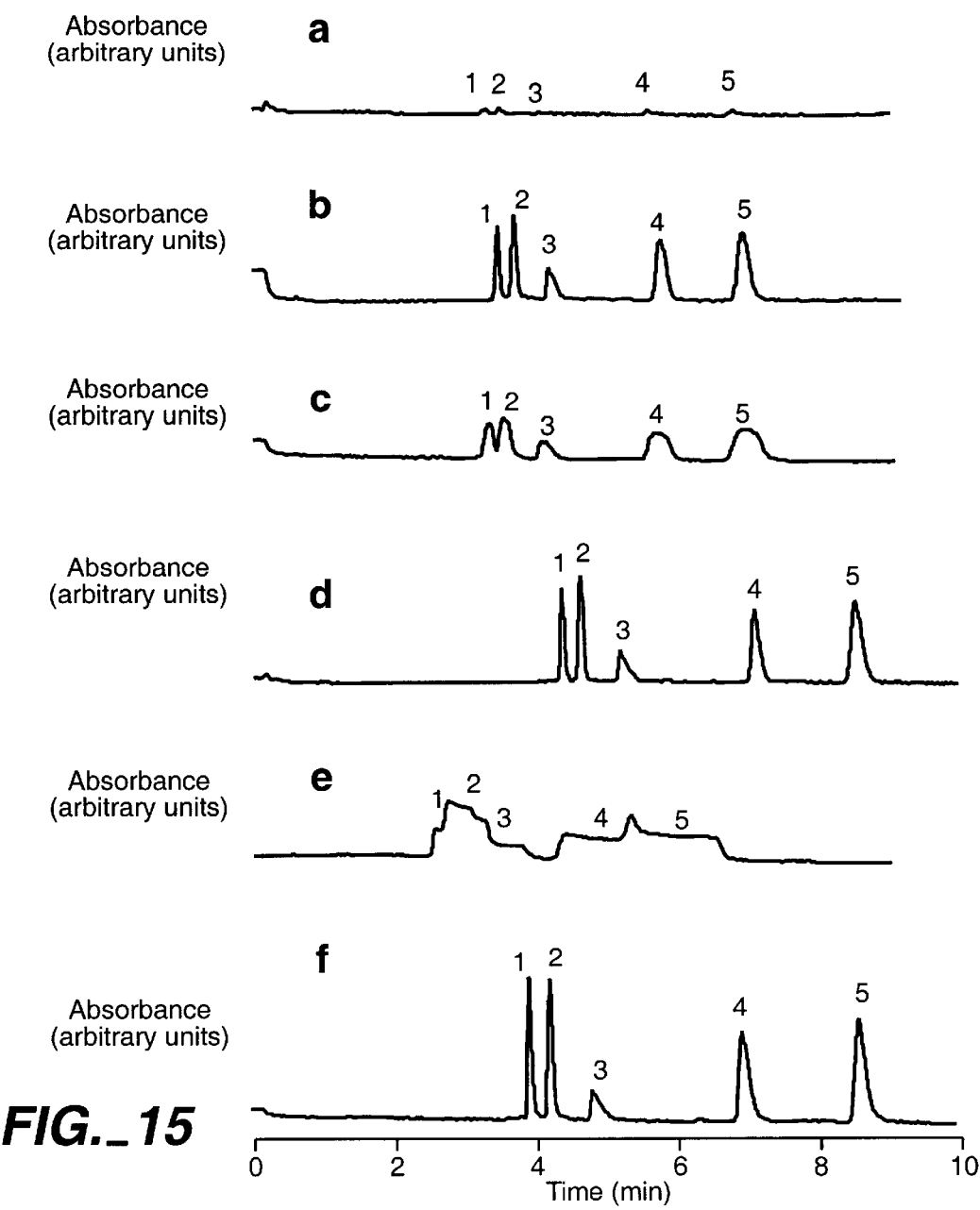
FIG._15

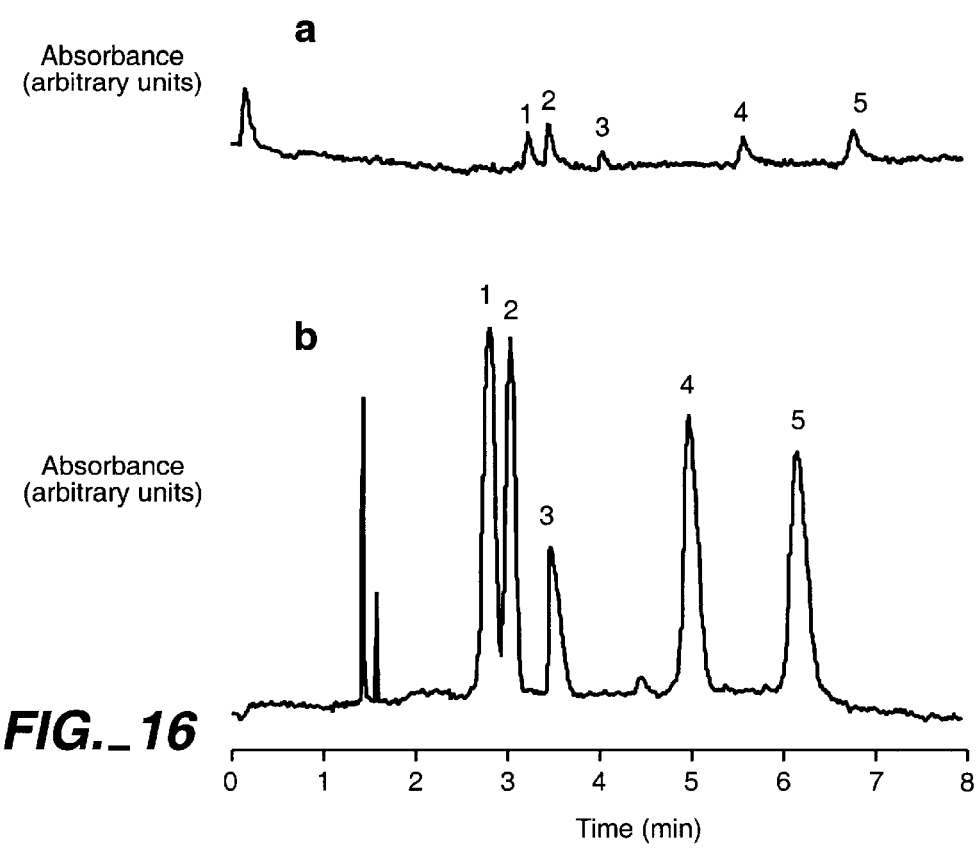
FIG._16

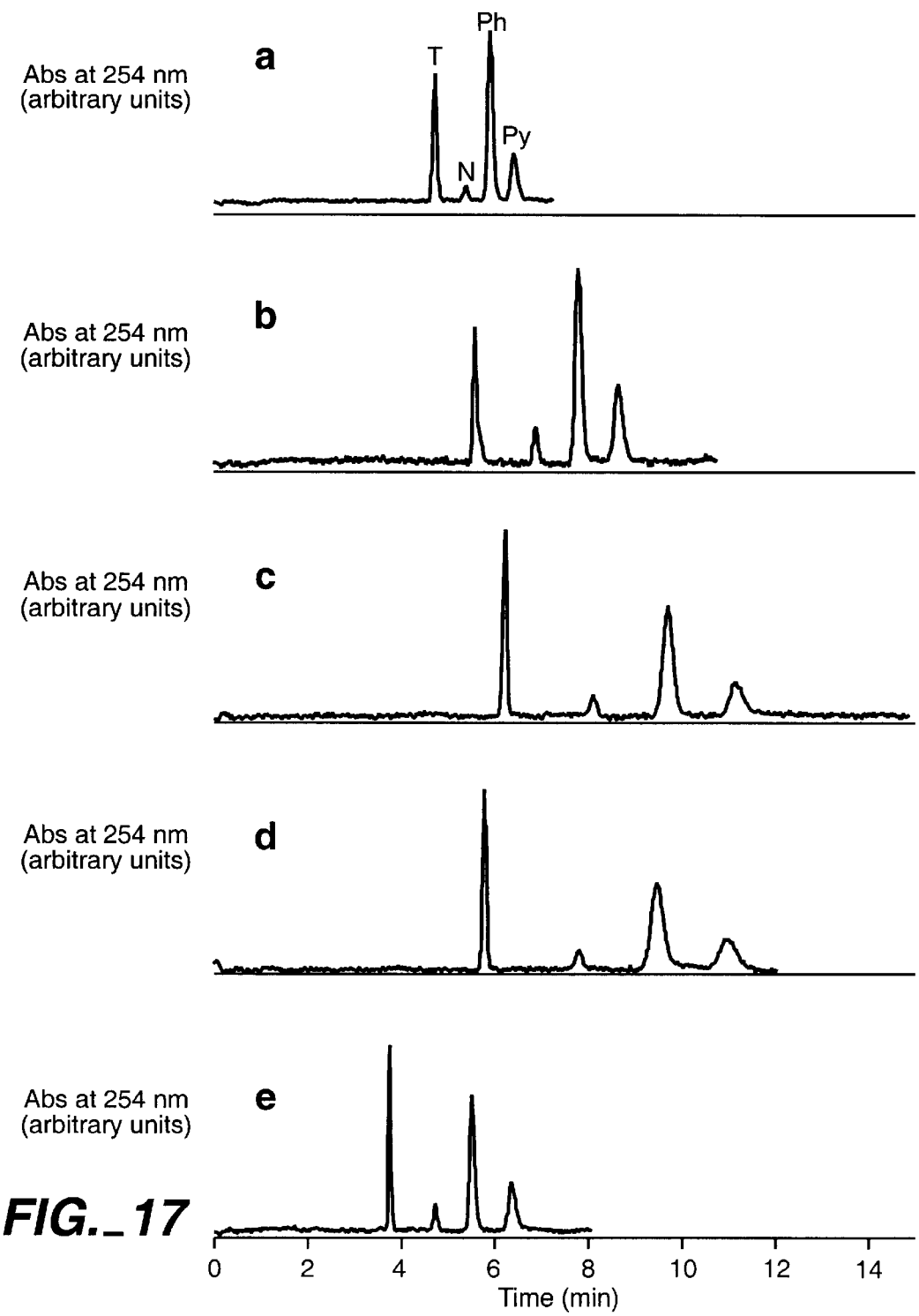
FIG._17

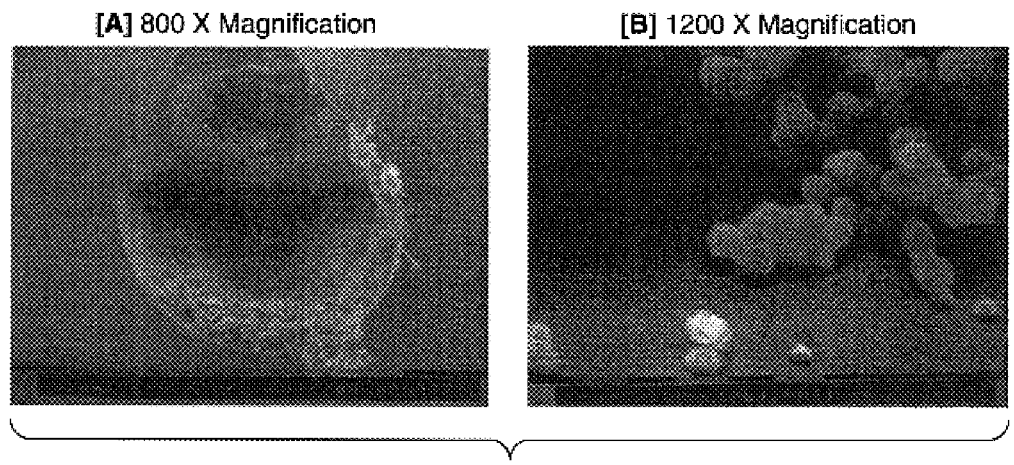
FIG._18
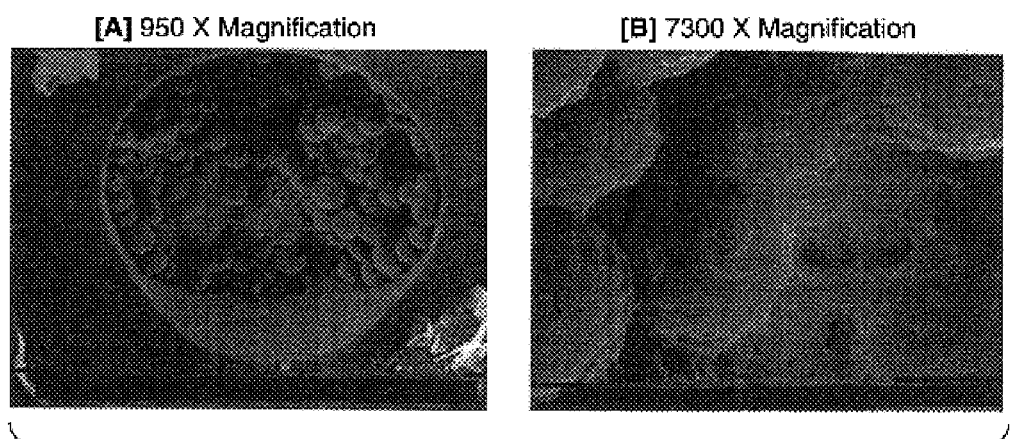
FIG._19
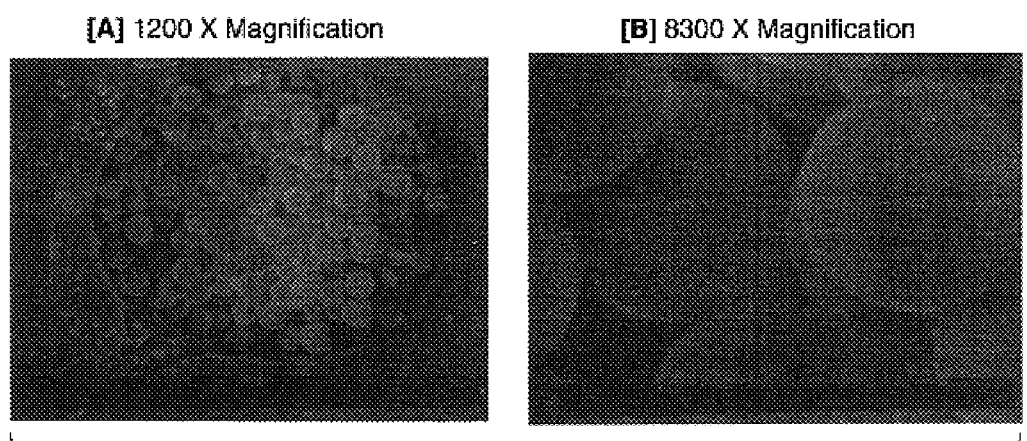
FIG._20

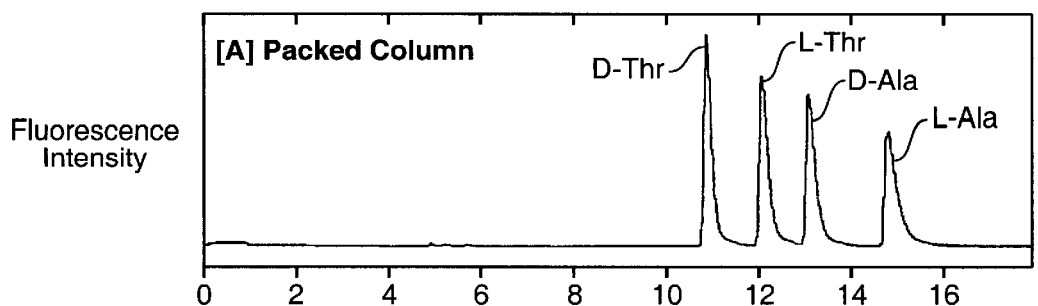
FIG._21A
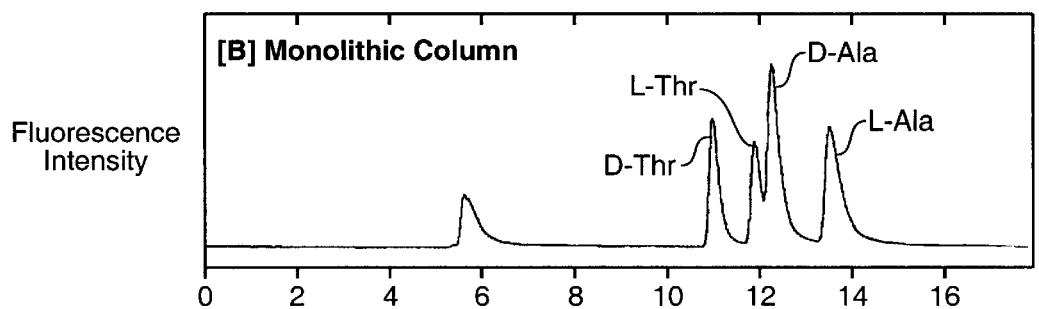
FIG._21B
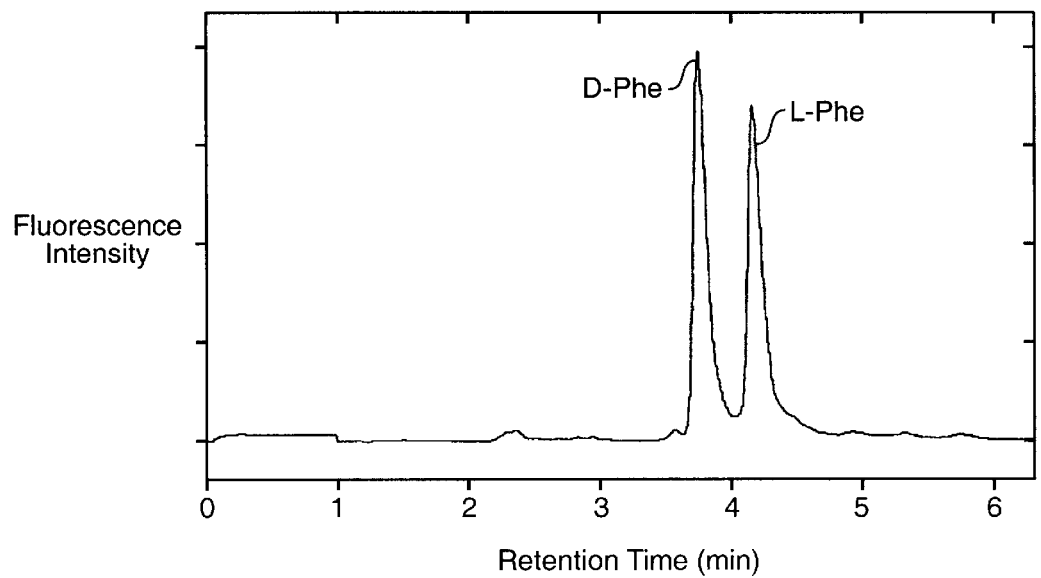
Retention Time (min)
FIG._22

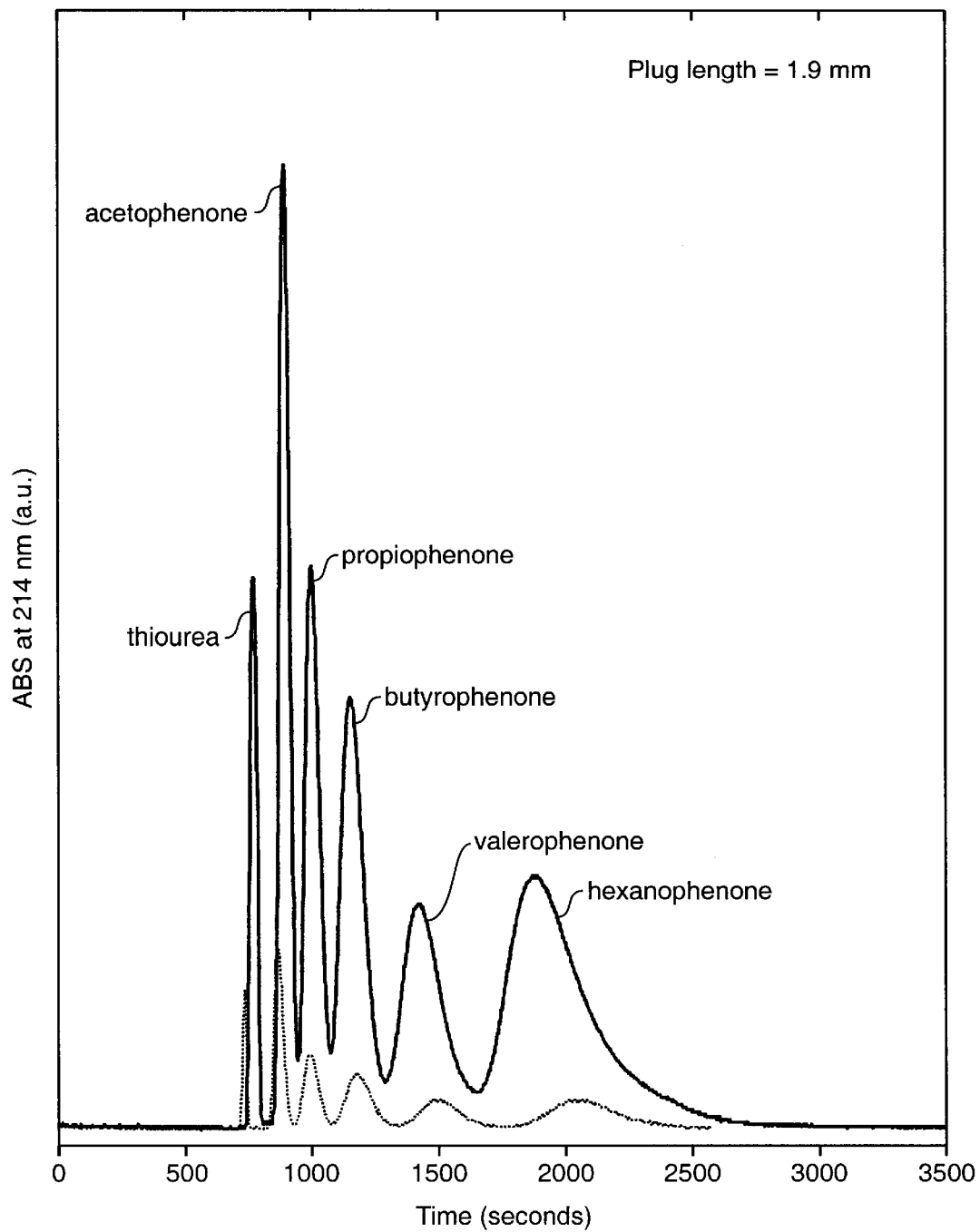
FIG._23

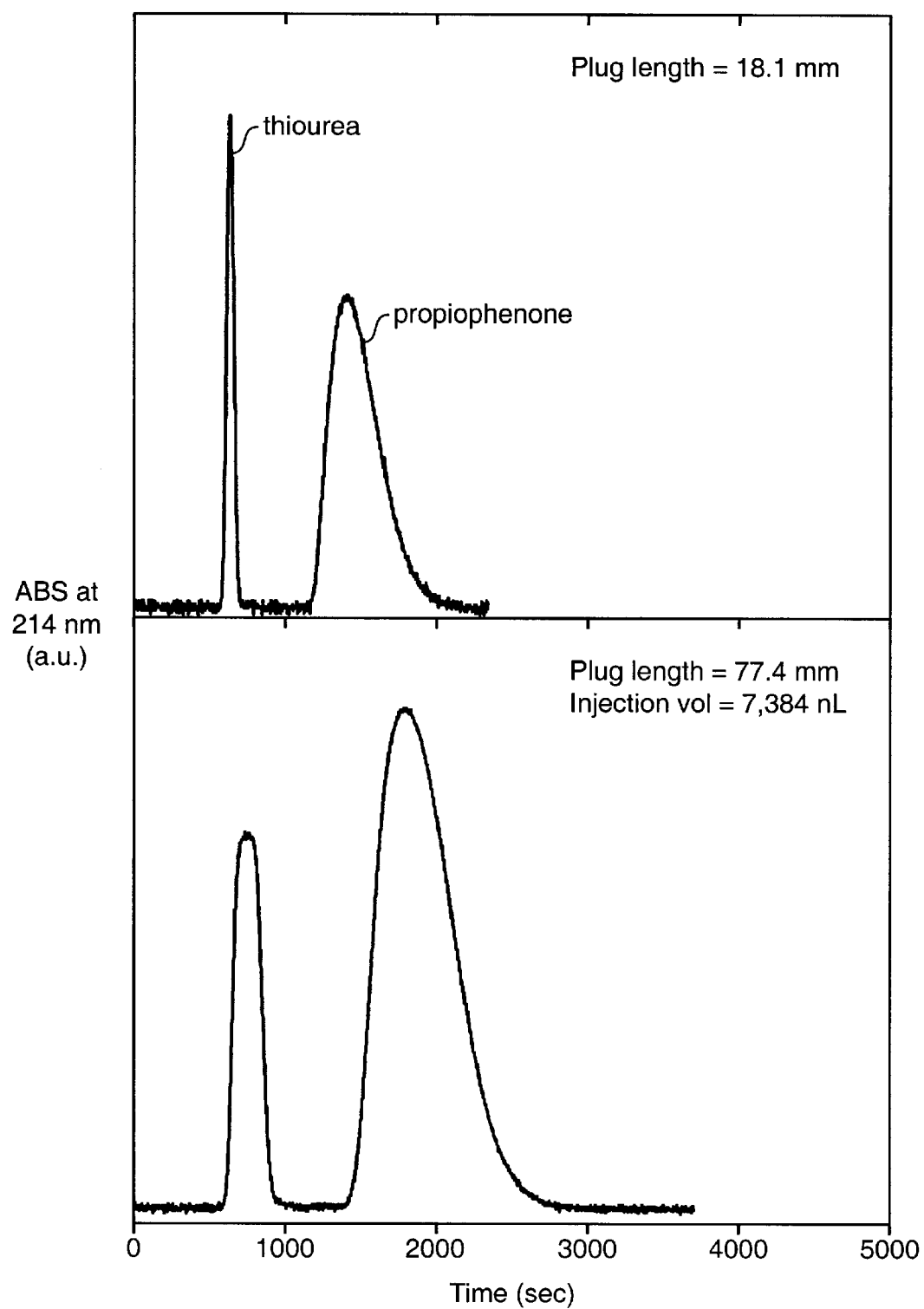
FIG._24

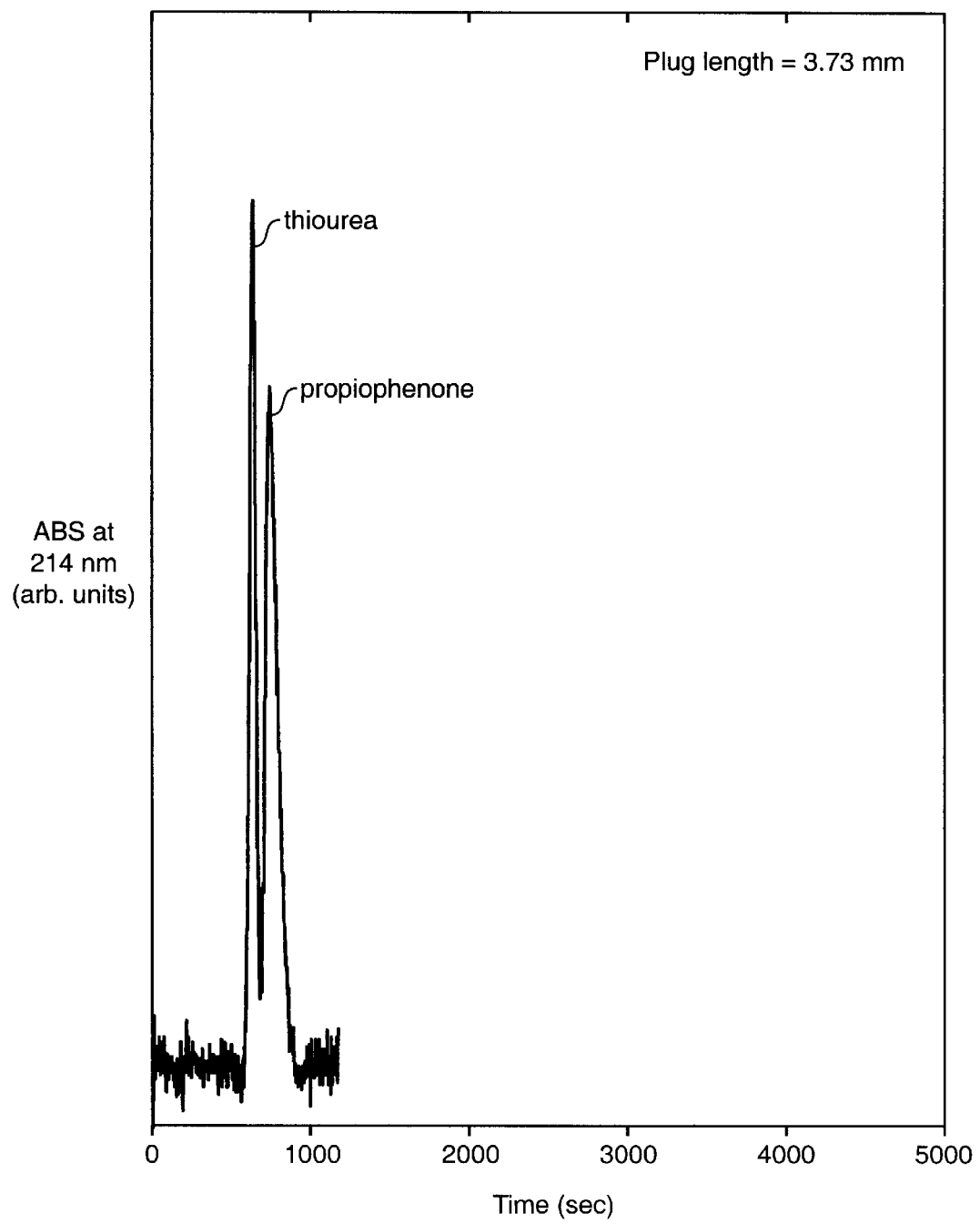
FIG._25

SEPARATION COLUMN HAVING A PHOTOPOLYMERIZED SOL-GEL COMPONENT AND ASSOCIATED METHODS

CROSS-REFERENCE TO RELATED APPLICATIONS

This application is a continuation-in-part of U.S. application Ser. No. 10/008,482, entitled "Fused-Silica Capillaries With Photopolymer Components," inventors Zare et al., filed Nov. 13, 2001, now abandoned, which is a continuation of Ser. No. 09/507,707, filed Feb. 18, 2000, now abandoned, both of which are expressly incorporated herein in their entirety by reference.

This application is also a continuation-in-part of U.S. application Ser. No. 09/929,275, entitled "Photopolymerized Sol-Gel Column and Associated Methods," filed Aug. 13, 2001, inventors Zare et al., now pending, which is expressly incorporated herein in its entirety by reference.

FIELD OF THE INVENTION

The invention relates in general to a separation column, and, in particular, to a separation column that includes a photopolymeized sol-gel component and associated methods.

BACKGROUND OF THE INVENTION

Over the past decade, capillary zone electrophoresis (CZE), with its high peak capacity (i.e., the number of peaks separated per unit time), has developed into a powerful and widely used technique for separating ionic species by their electrophoretic mobilities. The lack of selectivity for uncharged analytes in CZE, however, has remained more problematic. Several methods have been developed, such as micellar electrokinetic chromatography (MEKC), to help overcome this problem by providing a pseudostationary phase in which uncharged compounds can be separated. The application of methods such as MEKC is limited because of the restricted number of pseudostationary phases that can be employed in this technique.

With the advent of capillary electrochromatography (CEC), where both chromatographic and electrophoretic transport mechanisms are combined, separation and analysis of mixtures of uncharged analytes can be achieved using low sample volumes with high resolution and efficiency. The increased interest in CEC for analytical applications arises from the large plate numbers and relatively high separation speeds achieved and the wide range of stationary phases (those commonly used in high-performance liquid chromatography) that can be used.

Although CEC has been applied in many different areas, packed-column preparation and low-detection sensitivity remain challenges of this technique. Capillary columns containing small silica packings have been the mainstay of CEC. One disadvantage of packed columns is the fabrication of porous frits of controlled pore sizes, lengths, and high mechanical stabilities. Although systematic studies regarding the effects of the frits on the performance of such capillaries have not been reported, it is thought that these frits can degrade the efficiencies of these capillary columns.

Nevertheless, where separation columns are desired with packing material requiring frits, it would be desirable to have simple and reproducible procedures for fabricating frits. The conventional method of frit fabrication for a particle-packed column involves thermal sintering of a section of the packing material, such as octadecyl silica particles (ODS). This approach has several disadvantages, including (1) difficulty in generating the frit reliably and reproducibly, (2) alteration of the characteristics of the stationary phase within the frit itself, (3) difficulty in controlling the porosity of the frit, (4) weakness of the capillary at the location of the frit, (5) band broadening caused by the frit, (6) bubble formation and adsorption of polar analytes on the frit. These problems can directly affect the column performance and column-to-column reproducibility.

Alternative approaches have been reported for the preparation of capillary columns that avoid the technical problems of frit fabrication and column preparation associated with slurry and electrokinetic packing. One approach uses bonded stationary phases. Capillary columns prepared in this manner, however, suffer from low retention and low sample capacities as well as long preparation times. An alternative method for the preparation of open tubular capillary columns uses monolithic packing technology. For example, preparation and characterization of monolithic porous capillary columns loaded with chromatographic particles based on sol-gel chemistry have been described (see, e.g., Dulay et al., *Anal. Chem.*, 70, pp. 5103–5107, 1998). Monolithic capillary columns have received much attention because of the advantages offered in the control of permeability and surface charge.

A major challenge in CEC techniques is the detection of samples containing analytes at low concentration. The lack of sensitivity at low concentration stems from the small sample volume and the short optical path length for on-line detection. Dedicated sample preparation schemes that enrich the target analytes before sample injection are often necessary in order to obtain the necessary sensitivity for many real-world analyses. Schemes such as solvent-solvent extraction and solid-phase extraction are often very tedious and time-consuming.

An alternative to these schemes is on-line preconcentration. In gas chromatography, this goal is met by passing a gas stream through a cold column that is subsequently heated. In high-performance liquid chromatography (HPLC), this process is usually done by gradient HPLC in which the analytes are retained on the column much more strongly for the first solvent than for succeeding ones. On-line preconcentration has also enjoyed some success in electrophoretic separations. For example, in capillary electrophoresis (CE), these include isotachophoresis, sample stacking, sweeping, and the use of a dynamic pH junction. In CZE, it has been demonstrated that changes in electric field strength between sample and background solution zones can focus (i.e., stack), charged species (see, e.g., F. E. P. Mikkers, F. M. Everaerts, P. E. M. Verheggen, *J. Chromatogr.* 169 (1979), pp. 1–10 and R. L. Chien, D. S. Burgi, *Anal. Chem.* 64 (1992) pp. 489A–496A). In electrokinetic chromatography, it has been shown that micelles can act to concentrate (i.e., sweep) neutral and charged species (see, e.g., J. P. Quirino, S. Terabe, *Science,* 282 (1998) pp. 465–68 and J. P. Quirino, S. Terabe, *Anal. Chem.* 71(8) (1999) pp. 1638–44).

In CEC using particle (e.g., octadecyl silica) packed columns, focusing effects similar to that in gradient high performance liquid chromatography have been reported. These focusing effects were achieved using (1) step-gradient elution, (2) preparation of the sample in a noneluting solvent, or (3) injection of a water plug after sample injection. In M. R. Taylor, P. Teale, D. Westwood, D. Perrett, *Anal. Chem.* 69 (1997) pp. 2554–58, the authors were the first to report the use of a step-gradient for the preconcentration of steroidal samples in 1997. In D. A. Stead, R. G.

Reid, R. B. Taylor, *J. Chromatogr. A* 798 (1998) pp. 259–67, the authors achieved a 17-fold increase in the detection sensitivity of a mixture of steroids by preconcentration using a noneluting sample matrix. In Y. Zhang, J. Zhu, L. Zhang, W. Zhang, *Anal. Chem.* 72 (2000) pp. 5744–47, the authors also used a noneluting solvent for the preconcentration of benzoin and mephenytoin by a factor of 134 and 219, respectively. In C. M. Yang, Z. El Rassi, *Electrophoresis* 20 (1999) pp. 2337–42, the authors reported on the preconcentration of a dilute sample of pesticides using a short plug of water injected after a long plug of sample. In M. J. Hilhorst, G. W. Somsen, G. J. de Jong, *Chromatographia* 53 (2001) pp. 190–96, the authors demonstrated preconcentration of structurally related steroids using a noneluting matrix and step-gradient elution. Again in sensitivity of 7 to 9 times was reported. Similarly, in T. Tegeler, Z. El Rassi, *Anal. Chem.* 73(14) (2001) pp. 3365–72, the authors reported preconcentration of analytes in a mixture of carbamate insecticides using a combination of a noneluting matrix and step-gradient elution. The maximum allowable sample plug length was approximately 20 cm and a 500-fold sensitivity increase is achieved for carbofuran. A further increase in detection sensitivity was achieved by Zhang co-workers, who combined field-enhanced sample injection with solvent gradient elution. They demonstrated a 17,000-fold increase in peak height for a positively charged analyte, propatenene.

It is desirable to provide an easy to manufacture separation column with improved characteristics relative to the aforementioned methods.

SUMMARY OF THE INVENTION

According to an embodiment of the invention, a separation column includes a separation channel and a porous matrix in the channel. The porous matrix includes a metal organic photopolymer. In this embodiment, the porous matrix preferably contains no chromatographic particles and is generally homogeneous. In embodiments of the invention, the separation column can comprise a capillary column.

In another embodiment of the invention, the porous matrix can comprise a frit adapted to retain a separation medium in the channel. The frit can have a controlled porosity and can be derived from a photocurable, methacrylate-substituted silicate. Since photopolymerization is generally initiated by means of radiation, the position of the flit can be localized and the porosity reproducibly controlled.

In yet another embodiment of the invention, the porous matrix can comprise a separation medium adapted to preconcentrate and separate analytes without the presence of chromatographic particles. The separation medium can be fritless. It is believed that the separation medium may allow for the preconcentration and separation of larger volumes of analytes than a separation column using chromatographic particles.

The invention further includes methods for preparing a separation column. According to one embodiment of a method of the invention, a mixture is introduced into a capillary column. The mixture includes a metal organic compound. The mixture is then irradiated within the capillary column to form a solid, porous matrix via photoinitiated polymerization. In this embodiment, the porous matrix preferably contains no chromatographic particles. Preparation of a separation column without chromatographic particles is relatively easier than preparing a separation column with chromatographic particles.

The photochemical route to the preparation of the porous matrix has many advantages: (1) short preparation time, (2) control of the pore size, (3) control over the placement and length of the porous matrix, (4) high mechanical strength, and (5) avoidance of high temperatures that lead to cracking.

The invention also includes methods for separating a sample of analytes. In accordance with an embodiment of the invention, the method begins by providing a separation column comprising a separation channel and a separation medium located within the separation channel. The separation medium comprises a porous matrix, and the porous matrix is formed from a metal organic photopolymer and preferably contains no chromatographic particles. Next, a sample of analytes carried in a solution is passed through the column. The separation medium preconcentrates the analytes within the column. Then a solution is caused to flow through the separation column, thereby separating and eluting the analytes. The separation medium both preconcentrates and separates the analytes. In addition to the effect exerted by the separation medium, preconcentration can be further enhanced by a solvent gradient or sample stacking.

BRIEF DESCRIPTION OF THE DRAWINGS

The above and other features and aspects of the invention will become more apparent upon reading the following detailed description in conjunction with the accompanying drawings, in which:

FIG. 1A is a cross-sectional view of a separation column in accordance with an embodiment of the invention;

FIG. 1B is a perspective, schematic view of a separation column where the porous matrix acts as a separation medium according to an embodiment of the invention;

FIG. 1C is a perspective, schematic view of a separation column where the porous matrix acts as two frits designed to retain a separation medium in accordance with an embodiment of the invention;

FIGS. 2A and 2B are two representative electrochromatograms showing a plot of absorbance versus retention time for (a) one column and (b) another column, using an embodiment of the invention;

FIG. 3 is a representative chromatogram showing a plot of absorbance versus retention time using an embodiment of the invention;

FIGS. 4A and 4B are SEM micrographs of embodiments of the invention;

FIGS. 5A and 5B are representative electrochromatograms showing plots of absorbance versus retention time for different analytes using embodiments of the invention;

FIG. 6 is a representative electrochromatogram showing a plot of absorbance versus retention time using an embodiment of the invention;

FIG. 7 (panels a and b) are representative electrochromatograms showing plots of absorbance versus retention time using an embodiment of the invention;

FIG. 8 (panels a, b, and c) are representative electrochromatograms showing plots of absorbance versus retention time using an embodiment of the invention;

FIG. 9 (panels a, b, c, d, and e) are representative electrochromatograms showing plots of absorbance versus retention time using an embodiment of the invention;

FIG. 10 is a graphical representation showing a plot of the logarithm of peak height ratio versus the percentage of water in a sample using an embodiment of the invention;

FIG. 11 (panels a, b, and c) are representative electrochromatograms showing plots of absorbance versus retention time using an embodiment of the invention;

FIGS. 12A, 12B, and 12C are representative electrochromatograms showing plots of absorbance versus retention time using an embodiment of the invention;

FIG. 13 (panels a and b) are representative electrochromatograms showing plots of absorbance versus retention time using an embodiment of the invention;

FIG. 14 (panels a, b, c, d, and e) are representative electrochromatograms showing plots of absorbance versus retention time using an embodiment of the invention;

FIG. 15 (panels a, b, c, d, e, and f) are representative electrochromatograms showing plots of absorbance versus retention time using an embodiment of the invention;

FIG. 16 (panels a and b) are representative electrochromatograms showing plots of absorbance versus retention time using an embodiment of the invention;

FIG. 17 (panels a, b, c, d, and e) are representative electrochromatograms showing plots of absorbance versus retention time using an embodiment of the invention;

FIG. 18 is an SEM micrograph of an outlet frit prepared according to an embodiment of the invention;

FIG. 19 is an SEM micrograph of an inlet flit prepared according to an embodiment of the invention;

FIG. 20 is a micrograph of a section of a packed segment of a capillary prepared according to an embodiment of the invention;

FIGS. 21A and 21B are electrochromatogram of a sample of NBD-DL-alanine (Ala) and NBD-DL-threonine (Thr) on a packed column and a monolithic column respectively;

FIG. 22 is an electrochromatogram of NBD-DL-Phe on a packed segment column;

FIG. 23 is an electrochromatogram of the separation of thiourea and 5 alkyl phenyl ketones using a large i.d. capillary;

FIG. 24 is an electrochromatogram of the separation of thiourea and propiophenone using a large i.d. capillary; and FIG. 25 is a second electrochromatogram of the separation of thiourea and propiophenone using a large i.d. capillary.

For simplicity of description, like reference symbols are used for like or similar parts in this application.

DETAILED DESCRIPTION

Separation Column Having a Photopolymerized Sol-Gel (PSG) Component

FIG. 1A is a longitudinal cross-sectional view of a separation column 11 prepared in accordance with an embodiment of the invention. Separation column 11 includes a separation channel 13 within a capillary column 12, and a porous matrix 15 within separation channel 13. In different embodiments of the invention, separation column 11 can take on different forms, including but not limited to alternative types of tubes or planar chips, and can further include a detection window.

Capillary column 12 can have many different cross-sections, including but not limited to a circular cross-section. In an alternative embodiment, capillary column 12 can have an elongated cross-section. These and other cross-sections are possible for capillary column 12 and are within the scope of the invention. Capillary column 12 can be a round capillary typically made of fused silica. An internal dimension of the capillary can be in a range of between about 5 $\mu$m and 1000 $\mu$m. The inside diameter (i.d.) of the capillary can range between about 5 $\mu$m to 1000 $\mu$m, or from around 10 $\mu$m to around 1000 $\mu$m, and will more likely be in the range of 75 $\mu$m to 500 $\mu$m. As noted above, capillary column 12 can alternatively be a planar chip or confined space, such as a column confined by two sheets.

In another embodiment, shown in FIG. 1C, porous matrix 15 can be used as a frit 22 adapted to retain a separation medium within separation channel 13. Generally, two frits 22 are used to hold the separation medium, one being in inlet 22 and the other being an outlet frit. The separation medium in this embodiment (not shown in FIG. 1C) can comprise a variety of materials, including but not limited to packed, spherical ODS particles or chiral particles. The particles would be located between frits 22 in FIG. 1C. In this embodiment, porous matrix 15 tends to comprise a relatively shorter structure when compared to the embodiment of FIG. 1B where porous matrix 15 is used as the actual separation medium 20 itself.

In yet another embodiment, porous matrix 15 can be used as a solid-phase extraction material. In one example of this type of use, porous matrix 15 can function to separate proteins from salts in a biological material sample. This is beneficial because salts will often cause damage to instruments used to measure or analyze the proteins in the sample. And in yet another embodiment, porous matrix 15 can be used as a chemical reactor. For example, proteins can be retained on porous matrix 15, and enzymes can then be added to porous matrix 15 to react with the proteins. The resulting peptides can later be separated by porous matrix 15.

Porous matrix 15 fills at least a portion of separation channel 13 and can be attached to a channel wall 17 of separation channel 13. Preferably, porous matrix 15 is covalently bonded to channel wall 17. Unlike known separation mediums, porous matrix 15 is homogeneous and does not contain chromatographic particles. The use of a homogeneous separation medium is advantageous because, in some known applications, the use of chromatographic particles introduces unwanted broadening (i.e. lack of resolution). In other embodiments of the invention, porous matrix 15 can be broken up into two sections that are separated by another section, such as a monolith with a different pore size or surface charge.

According to an embodiment of the invention, porous matrix 15 is formed using a metal organic, or metalorganic, photopolymer, wherein the term metal organic, or metalorganic, refers to a material that comprises an organic ligand attached to a metal atom or a metalloid atom. (See Brinker, C. Jeffrey, et al., *Sol-Gel Science, The Physics and Chemistry of Sol-Gel Processing*, p. 2 (1990).) The precursor of this photopolymer can include a metal alkoxide, wherein the term metal alkoxide refers to a metal organic, or metalorganic, material, that has a metal-oxygen-carbon linkage or metalloid-oxygen-carbon linkage. (Id.) Herein, where "metal" is used in connection with a metal organic, or metalorganic, material, or in connection with a metal alkoxide, it encompasses metals and metalloids. The metal can be any of a number of metals or metalloids, including but not limited to aluminum, barium, antimony, calcium, chromium, copper, erbium, germanium, iron, lead, lithium, phosphorus, potassium, silicon, tantalum, tin, titanium, vanadium, zinc, and zirconium. For instance, if the metal chosen is the metalloid silicon, the corresponding metal alkoxide would be a silane. According to embodiments of the invention, the precursor can further comprise a photoactive group such as a methacrylate. For example, the precursor can be trimethoxysilypropyl methacrylate, also know as methacryloxy-propyltrimethoxy silane. In other embodiments, the photoactive group can be a different acrylate or any other suitable other photoactive group.

Different functionalized or derivatized monomers can be used in the formation of porous matrix 15. The choice of monomer affects the physical properties of porous matrix 15, such as pore size, pore shape, polymer charge density, and hydrophobicity. Control of the pore sizes and shapes through the use of different porogens can result in porous matrix 15 having a wide distribution of pore sizes (i.e. apore-size gradient).

Photopolymerized Sol-Gel (PSG) Separation Medium

According to an embodiment of the invention, porous matrix 15 can comprise a separation medium. Generally, when porous matrix 15 is used as a separation medium, there is no need for frits within separation channel 13 to hold the separation medium in place. Porous matrix 15 as a separation medium tends to have an affinity for analytes and can be used to both preconcentrate and separate a sample of analytes. The affinity for an analyte can be described by the retention factor, k, of the analyte. The retention factor, k can be determined by the following equation:

$$k = \frac{\text{amount of component in stationary phase}}{\text{amount of component in mobile phase}}. \quad (1)$$

The retention factor k can also be expressed as:

$$k = \frac{t_R - t_O}{t_O}, \quad (2)$$

where $t_R$ is the migration time of the analyte, and $t_O$ is the migration time of an "unretained" analyte. The retention factor is affected by the nature of the solvent, the nature of the analyte, the length of the column, the permeability of the porous matrix, the hydrophobicity of the porous matrix, and the detailed morphology of the porous matrix.

Separation column 11 can be used for many different purposes, including analytical or semipreparative work. Separation of analytes into submilligram to milligram quantities may become possible with preconcentration on separation column 11. For instance, more than about 100 nL of sample solution at analyte concentrations in the mM levels can be injected into the column without significant evidence of overloading.

As noted above, control of the pore sizes and shapes through the use of different porogens can result in porous matrix 15 having a pore-size gradient. A separation medium formed from porous matrix 15 with a pore-size gradient can function as "molecule sorter" in capillary electrophoresis and capillary electrochromatography. Such a separation medium can separate a mixture of large molecules whose size structures or chemistries (e.g., DNA fragments) may differ. In addition, separation columns 11 can be designed for reversed-phase, size-exclusion, affinity, ion-exchange chromatographies, etc. Alternatively, a separation medium formed from porous matrix 15 can be a mixed phase porous matrix prepared from a mixture of monomers. For example, the monomers can include methacryloxypropyltrimethoxy silane, bis(triethoxysilyl)ethane, and bis(triethoxysilyl) octane. The mixed phase porous matrix can have different properties, such as hydrophobicity.

Photopolymerized Sol-Gel Frit

According to another embodiment of the invention, porous matrix 15 can be used to form photopolymer frits in capillary columns. The photopolymer method has several advantages over the existing sintered silica methods, including (i) easy and rapid preparation, (ii) short reaction times at room temperature, (iii) UV transparency of the photopolymer, (iv) fine control of pore sizes, and (v) control of frit lengths and frit position.

In an embodiment of the invention, the photopolymer frits are prepared by photocuring a methacrylate-substituted silicate. Suitable photocured sol-gels are known in the art and are useful for practicing this aspect of the invention. Briefly, a monomer such as 3-(trimethoxysilyl) propyl methacrylate (MAPTMS) is irradiated to form a sol-gel matrix. In alternate embodiments, other suitable monomers include but are not limited to metal organic monomers, such as metal alkoxides. When the gel is cured, a hard porous glass is obtained.

A porogen can be used when creating a porous matrix 15 for use as a frit. In different embodiments, the porogen can be a solvent (e.g. toluene or a 1:1 mixture of hexane and toluene), a polymer, or an inorganic salt (e.g. sodium chloride powder or sodium sulfate). Examples of polymeric porogens include poly(methyl methacrylate) or polystyrene. Other porogens include, but are not limited to, benzene, acetonitrile, isooctane, hexanes, alcohols, tetrahydrofuran, and acetone. In accordance with an embodiment of the invention, a mixture of isooctane and toluene can be used as the porogenic solvent for the preparation of porous polymers based on methacrylate.

The pore sizes in porous matrix 15 can be controlled through the use of different porogenic solvents, and further by variations in the molar ratios of the monomers and the porogens. Pore sizes as large as 5.0 microns, and possible larger, can be formed using the methods of the invention.

Method of Preparing a Separation Column

The invention further includes methods of preparation for separation column 11. In embodiments of the invention, the methods use a round capillary column 12 typically made of fused-silica to form separation column 11. The inside diameter (i.d.) of capillary column 12 can range from around 10 μm to around 1000 μm, and is preferably going to be from around 75 μm to around 500 μm.

According to one embodiment of a method of the invention, porous matrix 15 is formed within capillary column 12 using a mixture that generally comprises a metal organic monomer, a porogen, and a photoinitiator. The mixture is introduced into capillary column 12 used to form separation column 11, and can be introduced by using a syringe to flow the mixture through capillary column 12. The ends of capillary column 12 can then be sealed.

The mixture forms a solid, porous matrix after photoinitiated polymerization is performed. The metal organic monomer used in the mixture can be a metal alkoxide, such as a silane, or a mixture of metal alkoxides. The metal can comprise any of, but is not limited to, the following: aluminum, barium, antimony, calcium, chromium, copper, erbium, germanium, iron, lead, lithium, phosphorus, potassium, silicon, tantalum, tin, titanium, vanadium, zinc, or zirconium. The metal alkoxide can include a photoactive group such as methacrylate. In one embodiment, the precursor (here the metal alkoxide and photoactive group) can comprise trimethoxysilylpropyl methacrylate, also known as methacryloxypropyltrimethoxy silane. In another embodiment, the precursor can be a combination of methacryloxypropyltrimethoxy silane and another precursor, such as bis(triethoxysilyl)ethane or bis(triethoxysilyl) octane.

In embodiments of the invention, the metal alkoxide can be added to antacid or base catalyst for the hydrolysis of the precursor. The catalyst converts the alkoxy groups to hydroxyl groups. For example, a silane can undergo the following hydrolysis reaction to form a fully hydrolyzed silane:

$$Si(OR)_4 + 4H_2O \rightarrow Si(OH)_4 + 4ROH \quad (3).$$

The hydrolysis reaction can stop at a partially hydrolyzed silane, $Si(OR)_{4-n}(OH)_n$. The metal organic monomer and the catalyst can be stirred for a period of time, often ranging anywhere from a few seconds to twenty-four hours.

As noted above, the mixture also comprises a porogen or a mixture of porogens. The porogens can be mixed with the metal organic monomer and the catalyst, and the mixture can be stirred for period of time, again ranging anywhere from a few seconds to twenty-four hours. During this time, the metal organic monomer tends to undergo a condensation reaction to form dimers, trimers, and other oligomers. For example, a partially hydrolyzed silane can undergo the following condensation reaction:

$$2(RO)_3SiOH \rightarrow (RO)_3Si\text{—}O\text{—}Si(OR)_3 + H_2O \quad (4).$$

Larger oligomers can be formed by increasing the temperature of the reaction.

The porogen provides a molecular template to form pores within porous matrix 15. For example, as described above, the porogen can be a solvent, a polymer, or an inorganic salt. Solvents that can be used include toluene or a 1:1 mixture of hexane and toluene; polymers that can be used include poly(methyl methacrylate) or polystyrene; and inorganic slats that can be used include sodium chloride powder or sodium sulfate. The porosity (i.e. pore size and shape) of porous matrix 15 can be controlled by the type of porogen used and its volume or concentration in the reaction solution. For example, a molar or volume ratio of monomer to porogen can be selected to form pores in the mixture. By adjusting the molar ratio of the monomer and porogen, the physical properties (e.g., pore sizes) of porous matrix 15 can be controlled.

The polymerization process begin when the mixture is irradiated, and the photoinitiator or photoactive group on the monomer absorbs radiation from the radiation source. This starts a photochemical reaction which catalyzes the polymerization of the metal organic compound to form a homogeneous porous matrix 15 within capillary column 12. Capillary column 12 can be exposed to radiation for a short period of time, such as about five minutes. The radiation can include visible or ultraviolet light, and the wavelength of the radiation is dependent on the type of photoinitiator or photoactive group used in the reaction. If capillary column 12 used to form separation column 11 has an outer coating that is not transparent to the light source, the coating is first removed to make an irradiation window. The length of the coating will determine the length of porous matrix 15 formed within the separation column.

The photoactive group methacrylate can be photopolymerized at a wavelength of around 300 nm or 365 nm, as reported in C. Yu, F. Svec, J. M. J. Frechet, *Electrophoresis* 21(1) (2000) pp. 120–27 and H. G. Woo, L. Y. Hong, S. Y. Kim, S. H. Park, S. J. Song, H. -S. Ham, *Bull. Korean Chem. Soc.* 16 (1995) pp. 1056–59, respectively. In other embodiments, the photoinitiator used can be Irgacure 1800, which is photopolymerized at a wavelength of around 365 nm. Irgacure 1800 is available from Ciba Geigy, Tarrytown, N.Y.

The photochemical route to the preparation of porous matrix 15 has many advantages over other known methods of forming matrices, including a short preparation time, fine control over the pore size of the matrix, control over the placement and length of porous matrix 15, high mechanical strength, and avoidance of high temperatures that can lead to cracking of capillary column 12 or matrix. Furthermore, a porous matrix 15 formed according to the methods of the invention does not require frits or chromatographic particles, so the preparation of separation column 11 is easier than preparation of known separation mediums using frits or chromatographic particles.

In embodiments of the methods of the invention, an organic solvent can be passed through separation column 11 after porous matrix 15 is formed to remove any unreacted material, porogens, and photoinitiators. One such organic solvent that can be used is ethanol. The solvent can be flowed through separation column 11 using a syringe or other means.

Separation column 11 can also be conditioned with a separation solution before using separation column 11 for separating analytes. The separation solution can comprise a buffer, such as aqueous ammonium acetate, and an eluting solvent, such as acetonitrile.

Method to Separate a Sample of Analytes

The invention also includes methods to separate a sample of analytes. First, the analytes are preconcentrated on separation column 11. This is done by passing a sample of analytes contained within a sample solution through separation column 11. Analytes can include neutral species such as polycyclic aromatic hydrocarbons, alkyl benzenes, alkyl phenyl ketones, and steroids, and charged species such as peptides. The sample solution can comprise a buffer, such as aqueous ammonium acetate, and an eluting solvent, such as acetonitrile.

The sample solution can be passed through separation column 11 by applying a pressure or a voltage. If a pressure is used, the applied pressure typically ranges from 0 p.s.i. to as large as 20 p.s.i. on most separation columns 11. Much larger pressures can also be used with separation column 11 if necessary, particularly when a separation column 11 with a relatively large inside diameter is used. The pressure can be applied for various periods of time, ranging from one second to over half an hour. If a voltage is used, a field strength of around 40 V/cm can be applied to most separation columns 11 for a period of time. It should be noted that the specific pressure or voltage used will vary based on a number of factors, including the design of the separation column that is used. The injection plug length can also vary, and plug lengths of over two centimeters can be injected into separation column 11.

As the sample solution passes through separation column 11, porous matrix 15 preconcentrates the analytes on the column. The extent of preconcentration is purely dependent on the retention factor, k. The retention factor is affected by a variety of factors including the nature of the solvent, the nature of the analyte, and the detailed morphology of the separation medium. The flow rate minimally affects the extent of preconcentration.

The highly porous nature of porous matrix 15 results in a high mass transfer rate for the analyte, which facilitates the preconcentration effect. The high mass transfer rates arise from the enhanced accessibility of the analytes to the binding sites of the porous structure. Because of the high mass transfer rates, the kinetics of analyte-porous matrix interaction (i.e., the partitioning of the analyte between the mobile and stationary phases) is not the rate-limiting step in the separation. The high mass transfer rate distinguishes this separation method from previous forms of chromatographic separations. With this separation method, because of the high mass transfer rate, it is possible to inject and concentrate larger volumes of sample solution than in columns containing normal chromatographic materials.

The total preconcentration effect is directly proportional to the retention factor k, with longer injection plug lengths (e.g. greater than about 25 mm) leading to severe peak broadening of analytes having low k values. This behavior implies that there is a maximum length of sample plug for each analyte before peak shape becomes compromised.

A major advantage of on-line preconcentration is that it lowers the detection limit for a given analyte. Another advantage is that when porous matrix 15 is used for solid-phase extraction, preconcentration can be used to clean up the analytes from possible interfering species found in the sample matrix.

After the preconcentration phase, a separation solution is passed through separation column 11 to separate and elute the analytes. The separation solution can be passed through separation column 11 using the same techniques as described above for the sample solution, namely, by applying a pressure or a voltage. Again, the applied pressure can range from around 0.5 p.s.i. to around 20 p.s.i. on most separation columns for periods of time typically ranging from one second to over half an hour. If a voltage is used, a field strength of around 40 V/cm can be applied to most separation columns 11 for a period of time. As noted above, the specific pressure or voltage used will vary based on a number of factors, including the design of the separation column that is used.

The separation solution can comprise a buffer, such as aqueous ammonium acetate, and an eluting solvent, such as acetonitrile. In one embodiment, the separation solution is the same as the sample solution.

Porous matrix 15 acts to extract the analytes from solution as well as provides the stationary phase for chromatographic separation of the analytes. It is this extractor-separator combination that gives this method an advantage over known methods. For example, sample solution with plug lengths of over two-centimeters can be loaded into separation column 11 and preconcentrated using a separation solution that is the same as the sample solution.

In one embodiment, in addition to the effect exerted by porous matrix 15, a solvent gradient can be used to further enhance preconcentration of the analytes. In this embodiment, the sample can be dissolved in a solution with a higher concentration of a buffer (e.g., water) than in the separation solution. The higher concentration of the buffer in the sample solution increases the affinity of the sample to the stationary phase. When a solvent gradient is used, the plug length can be longer than the length of separation column 11. For example, using the invention, it was found that the injection of a 91.2-cm plug, which was more than three times the total length of the capillary, was possible with only a minor loss in resolution. Improvements in peak heights obtained under gradient conditions can be more than a thousand-fold.

For neutral analytes, two approaches exist for using gradients on porous matrix 15. The first approach is to increase the organic solvent ratio between the separation solution and the sample solution. The second approach is to increase the retention factor k in the separation by increasing the percentage of water in the separation solution while maintaining a reasonable percentage of organic solvent between the separation solution and the sample solution. Analysis is faster with the first approach, whereas the resolution is better with the second one.

In another embodiment of the invention, in addition to the effect exerted by the porous matrix, sample stacking can be used to further enhance the preconcentration of analytes. Sample stacking is the focusing of charged analytes when analytes pass the concentration boundary that separates regions of high and low electric field strengths. The high electric field zone is a lower conductivity sample solution containing more of the eluting solvent, whereas the low electric field region is a higher conductivity separation solution. The eluting solvent, such as acetonitrile, has a lower conductivity than the buffer, such as aqueous ammonium acetate. Thus, a higher concentration of the eluting solvent results in lowering the sample matrix conductivity.

In sample stacking, separation column 11 is prepared with the separation solution. When analytes are introduced into the separation column and a voltage is applied, the analytes in the sample solution at the inlet of the column rapidly accelerate toward the separation solution (lower electric field strength) already in the column, where on crossing the boundary between the sample solution and the separation solution, they slow down and stack into narrow zones at the interface.

Sample stacking is basically caused by the change in electrophoretic velocity at the concentration boundary. Electrophoretic velocity is the product of electrophoretic mobility and electric field strength. Focusing occurs (sample stacking) when the electrophoretic velocity decreases at the concentration boundary. Sample stacking is also explained using the fundamentals of isotachophoresis and Kohlrausch rules.

There are two approaches to perform sample stacking on porous matrix 15. The first approach is to increase the percentage of organic solvent, such as acetonitrile. The second is to decrease the concentration of the buffer component in the sample solution. Increasing the percentage of acetonitrile or other suitable organic solvent is especially useful for real samples containing high concentration of salts. Desalting, for example by dialysis, is therefore not necessary to make a lower conductivity solution for injection. Use of organic solvents is also useful for biological samples when deproteination is part of the sample preparation.

Separation of Large Volume Samples of Analytes

When dealing with the separation of analytes in a large volume sample, known separation techniques have many associated problems. For instance, capillary electrophoresis (CE) is not widely used as a preparative separation tool because of the low sample volumes and short detection path lengths inherent in the use of small inside diameter (i.d.) capillaries associated with CE. Loading of nanomolar quantities of analytes has only been realized in CE by using strategies such as multiple injections with fraction collection and bundled capillaries. One of the major drawbacks associated with attempting to use larger i.d. capillaries (200-$\mu$m i.d. and larger) is the generation of Joule heat.

CEC can be used to separate analytes in a large volume sample using large i.d. capillaries filled with small diameter chromatographic particles. For instance, a capillary with an inside diameter of 500 $\mu$m and filled with 1 $\mu$m spherical silica particles can be used. The silica particles are effective in at least some instances at dissipating the Joule heat generated in the column upon application of high voltage. Unfortunately, the large back-pressure of the particle-filled column often prevents high loading of a sample.

The use of the present invention in conjunction with larger i.d. capillaries has been shown to be useful in semipreparative, applications. In one embodiment of the invention, separation column 11 is constructed using a capillary with a relatively larger inside diameter (e.g. >500

μm). To separate large volume samples, the analytes are first preconcentrated on the separation column 11 of this embodiment. It has been shown that this technique allows for loading of up to at least 8 nanograms (ng) of analytes (e.g., propiophenone) in a porous matrix 15 filled 540 μm i.d. capillary.

The invention is described in more detail by the way of the following examples. The following examples are presented solely for the purpose of further illustrating and disclosing the invention, and are not to be construed as limiting the invention. Examples 1 through 17 discuss PSG separation mediums, example 18 discusses PSG frits, and example 19 discusses a PSG separation medium using a large i.d. diameter capillary column.

EXAMPLE 1

Materials and Chemicals. Fused-silica capillaries (75-μm i.d.×365-μm o.d.) were purchased from Polymicro Technologies, Phoenix, Ariz. Methacryloxypropyltrimetoxysilane (MPTMS) was purchased from Gelest, Tullytown, Pa. and Sigma-Aldrich, Milwaukee, Wis. and was used without purification. HPLC-grade toluene, phenanthrene, pyrene, alkyl benzene ketones, and steroids were purchased from sigma-Aldrich, Milwaukee, Wis. Irgacure 1800 was received from Ciba, Tarrytown, N.Y.

Instrumentation. A Beckman P/ACE 2000 capillary electrophoresis instrument with a UV-absorbance detector was used to carry out all CEC experiments. An XL-1500 UV cross-linker, available from Spectronics Corp., Westbury, N.Y., equipped with six 15 W blacklight tubes of predominantly 365-nm wavelength was used to irradiate the reaction solutions. Scanning electron microscopy (SEM) analyses were performed on a Philips SEM 505 scanning electron microscope, available from Eindhoven, Netherlands.

Polymerization Procedure. The monomer stock solution was prepared just prior to use by adding 375 μL of MPTMS to 110 μL of 0.12 N HCl. This solution was stirred at room temperature for approximately thirty minutes to afford a clear, monophasic solution. An appropriate amount of toluene (porogen) was added to the monomer stock solution, as shown below in Table 1.

TABLE 1

| Capillary Column | % toluene (v/v) |
|---|---|
| A | 90 |
| B | 80 |
| C | 75 |
| D | 73 |
| E | 65 |
| F | 50 |

The photoinitator, Irgacure 1800, was added first to the toluene as 5% of the total weight of the toluene/monomer stock solution. This photoinitator solution was then added to the corresponding amount of monomer stock solution, and stirred for thirty minutes at room temperature to afford a yellow, monophasic solution. To minimize the evaporation of toluene, the solution was prepared in a vial with a polysilicone cap through which the capillary was inserted during filling with the solution.

A 15-cm stripe of the polyimide coating on a 30-cm long capillary was removed using a razor blade positioned at 45° to the capillary surface. The mechanical stability of the capillary was remarkably good despite the removal of a stripe of polyimide coating. The irradiation light entered the capillary only through this 15-cm stripe. No monolith was formed in the capillary where the polyimide coating ("mask") remained intact.

Using a 0.5-mL disposable syringe, approximately 0.2 mL of the reaction solution was flushed through the capillary to wet thoroughly the wall surface before filling the capillary with the solution. This resulted in bonding of the monolith to the capillary wall. No special pretreatment of the capillary wall was necessary to bond the monolith to the wall. The filled capillaries were irradiated (900 mJ/cm$^2$) in a UV cross-linker using 365-nm light for five minutes to form the porous matrix.

After irradiation, the capillaries were washed with ethanol using a hand-held syringe to removed unreacted reagents or porogens. Because the monoliths were highly permeable, high pressures were not required to drive liquid through the capillaries. Once the unreacted reagents were removed, the monolith became opaque and could be viewed clearly through the capillary without the aid of a microscope. The homogenity of the porous matrix was confirmed at 100× magnification. Burning off the polyimide coating immediately after the monolith section with fuming sulfuric acid made a detection window.

Once fabricated, the capillary was successfully installed in the cartridge without any damage. The capillary was conditioned with the separation buffer for approximately five minutes using a syringe and a hand-held vise. Once in the instrument, the capillary was further conditioned by pressure rinsing (20 p.s.i.) with the separation buffer or by electrokinetically conditioning at 5 kV or 10 kV for thirty minutes.

Characterization. SEM was used to study the morphology of the separation column. A capillary was sectioned carefully to expose the monolith. The sectioned pieces of capillary were sputtered with gold prior to SEM analyses.

Analyte Separation. The analytes were prepared in the mobile phase to prevent gradient effects during the CEC experiments. The mobile phase was made up of various ratios (v/v) of 50 mM ammonium acetate, water, and acetonitrile. A new sample solution was used for every injection to maintain the same concentration of acetonitrile in the sample solution and the mobile phase.

FIG. 2A is a representative electrochromatogram showing a plot of absorbance versus retention time for column B. The separation was performed with a 50 mM ammonium acetate/water/acetonitrile (1/3/6) solution. The sample solution was injected at 0.5 p.s.i. pressure for three seconds, and the separation was performed with an applied voltage of 1 kV at a temperature of 20° C. and detected at 214 nm. The elution order of the separation was (1) thiourea, (2) tetrahydrofuran, (3) naphthalene, (4) phenanthrene, (5) fluoranthene, (6) pyrene, (7) 1,2-benzanthracene, and (8) 1,2,5,6-bienzanthracene.

FIG. 2B is a representative electrochromatogram showing a plot of absorbance versus retention time for column D. The separation was performed with a 50 mM ammonium acetate/water/acetonitrile (1/4/5) solution. The sample solution was injected at 0.5 p.s.i. pressure for three seconds, and the separation was performed with an applied voltage of 15 kV at a temperature of 20° C. and detected at 200 nm. The elution order of the separation was (1) benzene, (2) toluene, (3) ethylene benzene, (4) propyl benzene, (5) butyl benzene, and (6) hexylbenzene.

The elution order of the column was similar to that of reversed-phase chromatography with the larger molecular weight or more hydrophobic analytes eluting later than the smaller molecular weight or more hydrophilic analytes.

Elution of the analytes in both figures occurred in less than seven minutes. Bubble formation was not a problem during the CEC experiments, for which the typical operating currents were between 3 and 10 µA.

For a typical capillary column D, efficiencies of up to 100,000 plates/m are achieved for thiourea, a less-retained compound. Small variations in the elution times were observed for thiourea (0.65% RSD), naphthalene (1.10% RSD), phenanthrene (1.14% RSD), and pyrene (1.14% RSD) over a period of three days (n=33).

FIG. 3 is a representative electrochromatogram showing a plot of absorbance versus retention time for column D. The separation was performed with a 50 mM ammonium acetate/water/acetronitrile (1/3/6) solution. The sample solution was injected at 0.5 p.s.i. pressure for three seconds, and the separation was performed with an applied voltage of 1 kV at a temperature of 20° C. and detected at 214 mm. A sample of thiourea, napthalene, phenanthrene, and pyrene was separated within 110 minutes at an applied pressure of only 20 p.s.i. (the maximum limit of the instrument). Peak tailing was most severe for pyrene because of its strong interaction with the porous matrix, and tailing was not observed for thiourea, which has low retention on the column.

FIG. 4A is a scanning electron micrograph of the cross-section of a metal organic photopolymer formed with 80% (v/v) toluene (capillary B) in a 75-µm-i.d. capillary column. The micrograph showed an interconnecting network of 1-µm spherical structures through which micrometer-sized macropores (as large as 5 µm) are interspersed.

FIG. 4B is a scanning electron micrograph of the cross-section of a metal organic photopolymer formed with 50% (v/v) toluene in a 75-µm-i.d. capillary column. In contrast to the porous matrix shown in FIG. 4A, the structure shown in FIG. 4B was a dense photopolymer with macropores of 2 µm or less in diameter. Consequently, the matrix in FIG. 4B was less permeable, and a significant back pressure occurs. No liquid could be driven through the column at pressures near 200 p.s.i.

The permeability of a porous matrix was determined by the linear velocity of the porous matrix, which is proportional to permeability as described in Darcy's law. The permeability of a porous matrix as a function of the macropore size was highly dependent on the volume and type of porogen used to prepare the photopolymer. For a column made with 90% (v/v) toluene (column A), the linear velocity is 12.3 cm/min, and an 80% (v/v) column (column B) had a linear velocity of 3.3 cm/min, whereas a column made with 73% (v/v) toluene (column D) had a linear velocity of 0.6 cm/min. These linear velocity data suggested that the macropores decrease with decreasing porogen concentration. This behavior was consistent with what has reported in the literature.

EXAMPLE 2

The separation column was prepared as described in Example 1. A mixture of 1:1 hexane/toluene was used for the porogen. The separation column had a separation performance similar to that of a separation column made with 80/20 toluene/reaction solution. A column efficiency of 68,000 plates/m (RSD 7.0%, n=5) for thiourea and an electroosmotic flow (EOF) velocity of 3.7 cm/min was obtained.

EXAMPLE 3

A mixture of 375 µL of MPTMS and 100 µL of 0.12 M hydrochloric acid was stirred for thirty minutes at room temperature. 27 parts of this mixture were combined with 73 parts of toluene to give 200 µL of the final solution. 5% by weight of the final solution of the photoinitator Irgacure 1800 was added, and the resulting sol-gel solution was stirred for five minutes before use. A 75-µm i.d.×365-µm o.d. fused silica capillary was filled with the sol-gel solution, and the separation column was exposed to UV light in a Spectrolinker X1–1500 at 365 nm to affect photopolymerization. The polymerization length of the porous matrix was controlled by removing a 15-cm strip of the polyimide coating of the capillary prior to irradiation for five minutes. Unreacted reagents were flushed with ethanol. The total length of the capillary was 25.6 cm (18.8 cm from inlet to the detector window). The resulting column was conditioned with the separation solution prior to use.

All electrophoresis experiments were performed with a Beckman P/ACE 2000. The capillaries were thermostated at 20° C. Injections were done using pressure (i.e., 0.5 p.s.i. and 20 p.s.i.) or voltage (1 kV to 10 kV) and varied in duration from two seconds to 1920 seconds. Detection was done at 214 or 254 nm. Data analysis was performed with GRAMS/32 version 4.02, available from Galactic Industries Corporation, Salem, N.H.

FIGS. 5A and 5B are representative electrochromatograms showing plots of absorbance versus retention time using an embodiment of the invention. The figures illustrate the increase in detection sensitivity with an increase in injected plug length in the CEC separation of a mixture containing the small molecule, thiourea, three polycyclic aromatic hydrocarbons (PAHs), and eight alkyl phenyl ketones. To eliminate solvent gradient effects, the sample was prepared in the separation solution. The sample and separation solutions were 50 mM ammonium acetate/water/acetonitrile (1/4/5). In FIG. 5A, the plug lengths were 0.1 mm, 6.8 mm, 13.7 mm, 27.4 mm, and 34.2 mm. The 0.1 mm plug length was for an applied pressure of 0.5 p.s.i., whereas all other plug lengths were for an applied pressure of 20 p.s.i.. The applied voltage for the separation was 20 kV, and the absorbance was measured at 214 nm. The elution order of the column was (1) 12.5 µM thiourea, (2) 51.0 µM naphthalene, (3) 1.0 µM phenanthrene, and (4) 123 µM pyrene.

In FIG. 5B, the column was prepared in the same manner as the column as described earlier, except that the column was post-modified by continuous flow of (3,3,3-trifluoropropyl)trichlorosilane for thirty minutes at room temperature and followed by rinsing with toluene. The plug lengths were 0.7 m, 7.2 mm, 10.7 mm, 17.9 mm, and 28.6 mm. The applied voltage was 15 kV, and the absorbance was measured at 254 nm. The elution order of the column was (1) 5 µM thiourea, (2) acetophenone, (3) propiophenone, (4) butyrophenone, (5) valerophenone, (6) hexanophenone, (7) heptanophenone, (8) octanophenone, and (9) decanophenone. The concentration of each of the alkyl phenyl ketones was 0.1. µg/mL in the separation solution.

For the PAH mixture illustrated in FIG. 5A, the peaks were barely visible with the typical injection of a 0.1 mm plug length, but the peak heights increased when the plug length increased from 6.8 to 34.2 nm. Thus, the separation column, an embodiment of the invention, allowed for the injection of a longer plug length than a typical separation column does. Similarly, for the alkyl phenyl ketone mixture illustrated in FIG. 5B, the peak heights increased when the plug length was increased from 0.7 mm to 57.3 mm. As the plug length was increased, all four peaks showed increased broadening, but the later eluting peaks are more symmetrical to a small extent than the earlier ones. This behavior is backwards from what is observed in typical chromatographic separations in which the later eluting peaks are less symmetrical than the earlier ones because of dispersion effects. These results suggest that the analytes accumulate at the inlet of the poroux matrix during the injection, with the more retentive species being localized more effectively than the less retentive ones.

In FIG. 5A, the improvement in peak heights for a 27.4-mm injection compared to a typical injection of 0.1 mm is 50, 125, and 127 times for naphthalene, phenanthrene, and pyrene, respectively. The sample solution in the 27.4-mm injection is a 10-fold dilution of the sample in the typical 0.1-mm injection.

EXAMPLE 4

The separation column was prepared as described in Example 3. The sample and separation solution was 50 mM ammonium acetate/water/acetonitrile (1/3/6). The samples were injected at 1 kV. The applied voltage was 15 kV, and the absorbance was detected at 214 nm. FIG. 6 is a representative electrochromatogram of a plot showing absorbance versus retention time using an embodiment of the invention. 39.0 mM of naphthalene in the separation solution was injected for five seconds, as represented by signal a, and a 3.9 mM of naphthalene in the separation solution was injected for eighty-five seconds, as represented by signal b. The corrected peak areas (peak area/migration time) for both electrochromatograms were made close to each other by controlling the injection time of the ten-fold dilution of sample. The corrected peak areas of the electropherogram in lines a and b are 0.0023 (%RSD=0.02%, n=3) and 0.0025 (%RSD=0.00, n=3) arbitrary units/min, respectively. This comparison was done such that the amount of naphthalene molecules injected for each run is the same.

Preconcentration was evidenced by the slightly higher peak height for the longer injection of diluted sample and almost the same corrected peak widths (peak width/migration time) for both experiments, despite the different sample concentration. The peak heights of the electrochromatograms in signals a and b were 0.0869 (%RSD=0.36%, n=3) and 0.0937 (%RSD=0.06%, n=3) arbitrary units, respectively. The peak widths of the electrochromatograms in signals a and b were 0.0253 (%RSD=0.07%, n=3) and 0.0249 (%RSD=0.01%, n=3) arbitrary units/min, respectively. The shift in migration time on line b was caused by the longer injection time, which made the center of the sample plug closer to the detector window.

EXAMPLE 5

A mixture of 575 μL of MPTMS and 100 μL of 0.12 M hydrochloric acid was stirred for thirty minutes at room temperature. 20 parts of this mixture were combined with 80 parts of toluene to give 200 μL of the final solution. The photoinitiator was added as 10% of the total volume of the final solution, and the resulting sol-gel solution was stirred for five minutes before use. The separation column was prepared as described above in Example 3. Unreacted reagents were flushed with toluene. The surface of the porous matrix was modified by continuous flow of pentafluorophenyltrichlorosilane through the capillary for forty-five minutes at room temperature and followed by rinsing with toluene.

FIG. 7 (panels a and b) are representative electrochromatograms showing plots of absorbance versus retention time using an embodiment of the invention. The separation solution was 50 mM phosphoric acid/water/acetonitrile (1/5/4). The applied voltage was 15 kV, and the absorbance was detected at 214 nm. FIG. 7 (panel a) shows a 0.5 p.s.i. injection at 0.1 mm plug length of test peptides, and FIG. 7 (panel b) shows a 0.5 p.s.i. injection at 12 mm plug length of test peptides. The test peptides, which were charged analytes, were (1) bradykinin, (2) angiotensin II, (3) tripeptide I, (4) tripeptide II, and (5) methionine enkephalin. The concentration of the peptides were 16.7 μg/ml. The cathode directed velocities of the peptides were dictated by both electrophoretic and electroosmotic flow effects. The peptides had a net positive charge at the pH of the separation solution (pH=2). The improvement in peak heights for the longer injection compared to a typical injection of 0.1 mm plug length is 21, 19, 16, 18, and 22 times for bradykinin, angiotensis II, tripeptide I, tripeptide II, and methionine enkephalin, respectively. This result demonstrates the usefulness of this method for charged analytes.

EXAMPLE 6

The separation column was prepared as in Example 3. FIG. 8 (panels a, b, and c) are representative electrochromatograms showing plots of absorbance versus retention time using an embodiment of the invention. FIG. 8 shows an analysis of a urine sample, spiked with 0.1 mM hydrocortisone (peak 1), 0.3 mM progesterone (peak 2) and 0.2 mM cortisone (peak 3). Four parts of spike or unspiked urine were mixed with six parts of acetonitrile and centrifuged to remove proteins. One part of each supernatant was mixed with one part of 50 mM ammonium acetate/water/acetonitrile (1/7/2) before injection. FIG. 8 (panel a) shows an injection plug length of 0.1 mm, and FIG. 8 (panel b) shows an injection plug length of 21.4 mm. FIG. 8 (panel c) represents a 21.4-mm injection plug length of urine blank. The separation solution consisted of 50 mM ammonium acetate/water/acetonitrile (1/5/4). The applied voltage for the separation was 17 kV, and the absorbance was measured at 254 nm. After protein precipitation with acetonitrile, these steroids were detected and quantified with a 21.4-mm injection of the sample solution, but are weakly detected with a typical 0.1-mm injection. A comparison between the blank run and the spiked run showed that the sample matrix, which still contained other biomolecules, did not significantly interfere with steroid analysis on the separation column. This result demonstrates the usefulness of the technique for biofluid analysis.

EXAMPLE 7

The separation column was prepared as described in Example 3. FIG. 9 (panels a, b, c, d, and e) are representative electrochromatograms showing plots of absorbance versus retention time using an embodiment of the invention. Sample plug lengths of 1.1 cm were injected. The separation solution was 5 mM ammonium acetate in 60% acetonitrile, and the sample solutions were 5 mM ammonium acetate in 60% acetonitrile (panel a), 50% acetonitrile (panel b), 40% acetonitrile (panel c), 30% acetonitrile (panel d), and 20% acetonitrile (panel e). The applied voltage for the separation was 15 kV, and the absorbance was detected at 254 nm. The elution order was (1) thiourea, (2) acetophenone, (3) propiophenone, (4) butyrophenone, (5) valerophenone, (6) hexanophenone, (7) heptanophenone, (8) octanophenone, and (9) decanophenone. The concentration of each analyte was 2 nl/ml.

The retention factors, k, obtained for acetophenone (peak 2), propiophenone (peak 3), butyrophenone (peak 4), valerophenone (peak 5), hexanophenone (peak 6), heptanophenone (peak 7), octanophenone (peak 8), and decanophenone (peak 9) were 0.18, 0.25, 0.32, 0.41, 0.53, 0.67, 0.85, and 1.33, respectively. In this study, thiourea (peak 1) was used as the essentially unretained neutral solute for the determination of k. The value of k and migration time follows the increase in alkyl chain length. In general, the peak shapes and resolution improved when the water concentration was increased from 40% to 50%, 60%, 70%, and 80%, as evidenced by panels a, b, c, d, and e, respectively.

EXAMPLE 8

The experimentation conditions were the same as in Example 7. FIG. 10 is a graphical representation of a plot showing the logarithm of peak height ratio (peak height obtained from a higher concentration of water in the sample matrix divided by peak height obtained from a sample matrix similar to that of the separation solution) versus the percentage of water in the sample matrix. The data indicated that a limit exists to which the peak heights can be improved by increasing the concentration of the buffer in the sample matrix. Preconcentration was improved owing to the increased attraction of the analytes to the porous matrix. When the value for the logarithm of the peak height ratio was less than 1, about 1, or greater than 1 there was a decrease, no change, or increase, respectively, in peak height compared to a similar injection using the separation solution as the sample matrix. For all test APKS, peak heights improved when the water concentration was increased from 40% to 50% and from 50% to 60%. Peak heights did not improve when the percentage of water was increased from 60% to 70% or more, except for the two lowest k analytes (acetophenone and propiophenone) when the percentage of water was increased from 60% to 70%. Peak heights worsened for the higher k analytes (heptanophenone, octanophenone, and decanophenone) in the 80% water matrix. The reason for the decrease in peak heights is the decrease in the solubility of the high k analytes in the highly aqueous sample matrix. The corrected peak areas, which is a measure of the amount of sample loaded for octanophenone and decanophenone is 10% to 60% lower in the 80% water matrix compared to the other sample matrices used. To avoid solubility problems, the test APKs in succeeding experiments were prepared in matrices having at least 30% acetonitrile.

EXAMPLE 9

The separation column was prepared as described above in Example 3. FIG. 11 (panels a, b, and c) are representative electrochromatograms showing plots of absorbance versus retention time using an embodiment of the invention. The separation solution is 5 mM ammonium acetate in 60% acetonitrile. The plug lengths were 0.2 cm for a sample solution of 5 mM ammonium acetate in 60% acetonitrile (panel a); 2.74 cm for the same sample solution was used in panel a (panel b), and 2.74 cm for a sample solution of 5 mM ammonium acetate in 30% acetonitrile (panel c). Other conditions and identification of peaks are the same as in Example 7.

The gradient condition, as shown in FIG. 11 (panel c), showed improved resolution and peak shapes. Improvements in peak heights under the gradient condition illustrated in FIG. 11 (panel c) were 36, 35, 38, 41, 42, 38, 32, and 24 times for acetophenone, propiophenone, butyrophenone, valerophenone, hexanophenone, heptanophenone, octanophenone, and decanophenone, respectively. The %RSDs (n=5) of measured peak heights ranged from 0.9% to 2.5%. %RSDs (n=5) of migration time ranged from 0.3% to 0.5%. The procedure is therefore reproducible in a single column.

EXAMPLE 10

FIGS. 12A, 12B, and 12C are representative electrochromatograms showing plots of absorbance versus retention time using an embodiment of the invention. The plug lengths were 2.74 cm for sample solution of 5 mM ammonium acetate in 40% acetonitrile (FIG. 12A), 2.74 cm for sample solution of 5 mM ammonium acetate in 30% acetonitrile (FIG. 12B), and 5.48 cm for a sample solution the same as in FIG. 12B (FIG. 12C). The separation solutions were 5 mM ammonium acetate in 60% acetonitrile (FIG. 12A) and 5 mM ammonium acetate in 50% acetonitrile (FIGS. 12B and 12C). Other conditions and identification of peaks are the same as in Example 7.

The k values were higher in FIG. 12B than in FIG. 12A because of the high percentage of water in the separation solution. The analyte molecules were more attracted to the PSG phase at high percentages of water. The distribution constant K (number of moles of solute in the PSG phase divided by the number of moles of solute in the separation solution), which is directly proportional to k increases with increasing concentration of water in the separation solution. In FIG. 12B, the k values for acetophenone, propiophenone, butyrophenone, valerophenone, hexanophenone, heptanophenone, octanophenone, and decanophenone were 0.29, 0.47, 0.65, 0.92, 1.28, 1.76, 2.37, and 4.25, respectively. To maintain the gradient effect constant, the percentage of organic solvent ratio between the separation solution and sample matrix was kept at the same value for FIGS. 12A and 12B. For reasons still unknown, the result in FIG. 12B shows that for analytes with lower k values (acetophenone and propiophenone) there were slight increases in peak heights compared to FIG. 12A. For the other test solutes, there are some decreases in peak heights.

FIG. 12C illustrates what happens for a longer injection plug of 5.48 cm and a higher percentage of water in the separation solution. Improvements in peak heights were 31, 33, 55, 44, 44, 37, 29, and 19 times for acetophenone, propiophenone, butyrophenone, valerophenone, hexanophenone, heptanophenone, octanophenone, and decanophenone, respectively. As in FIG. 11 (panel c), the improvements in peak heights do not follow k, unlike in nongradient conditions. The improvements in peak heights were comparable to those obtained with a higher percentage of organic solvent between the separation solution and the sample matrix (FIG. 11, panel c). Note that the injection plug is two times shorter in FIG. 11 (panel c) than in FIG. 12C.

EXAMPLE 11

FIG. 13 (panels a and b) are representative electrochromatograms showing plots of absorbance versus retention time using an embodiment of the invention. The plug lengths were 0.22 mm (panel a) and 19.5 cm (panel b). The separation solution was 5 mM ammonium acetate in 60% acetonitrile. The sample solutions were: 5 mM ammonium acetate in 60% acetonitrile (panel a) and 36% acetonitrile (panel b). The sample concentrations were 11 to 53 µg/ml (panel a) and 1.1 to 5.3 µg/ml (panel b). The applied voltage was 30 kV, and the absorbance was detected at 214 nm. The elution order was thiourea (peak 1), naphthalene (peak 2), phenanthrene (peak 3), pyrene (peak 4), and benz(e) acephenanthylene (peak 5).

A solvent gradient improved detection of four PAHs, as shown in FIG. 13 (panel b). A high percentage of acetonitrile (60%) in the separation solution, a shorter PSG length (10 cm), and a high electric-field strength (781.3 V/cm) were used for faster analysis times. FIG. 13 (panel a) is a 0.22-mm typical injection of sample prepared in the separation solution. FIG. 13 (panel b) is a 19.5-cm injection using a gradient where the sample is in a 36% acetonitrile matrix, which provides a high percentage of organic solvent between the sample solution and the separation solution Longer than 1 9.5-cm plug lengths cause broadening of the naphthalene peak. It is interesting to note that the injection length is longer than the length from the inlet to the detector window. (18.8-cm). The faster eluting thiourea zone is actually observed during the sample injection. The thiourea zone is therefore at the detection window at the start of the separation voltage.

Improvements in peak heights for naphthalene (peak 2), phenanthrene (peak 3), pyrene (peak 4), and benz(e) acephenanthylene (peak 5) are 346, 437, 409, and 315 times, respectively. The sample concentrations in FIG. 13 (panel b) were 10-fold lower than in FIG. 13 (panel a). For naphthalene, phenanthrene, and pyrene, the values stated above are 6.9, 3.5, and 3.2 times better than that previously reported under nongradient conditions, respectively.

EXAMPLE 12

FIG. 14 (panels a, b, c, d, and e) are representative electrochromatograms showing plots of absorbance versus retention time using an embodiment of the invention. The plug lengths were 0.23 mm (panel a), 7.6 cm (panel b), 22.8 cm (panel c), 45.6 cm (panel d), and 91.2 cm (panel e). The separation solution was 5 mM ammonium acetate in 60% acetonitrile. The sample solutions were: 5 mM ammonium acetate in 60% acetonitrile (panel a) and 40% acetonitrile (panels b, c, d, and e). The sample concentrations were 9 to 50 $\mu$g/ml (panel a), 0.9 to 5 $\mu$g/ml (panels b, c, d, and e). The applied voltage was 22 kV, and absorbance was detected at 254 nm. The elution order was thiourea (peak 1), decanophenone (peak 2), and pyrene (peak 3).

The peak heights of decanophenone (peak 2) and pyrene (peak 3) increased with increasing plug lengths. The injection was increased from 0.23 mm (panel a) to 7.6 cm (panel b), 22.8 cm (panel c), 45.6 cm (panel d), and 91.2 cm (panel e), which corresponds to 0.1%, 30%, 89%, 178%, and 356% of the total capillary length. The high porosity or the low resistance to flow of the porous matrix made it possible to introduce increasing lengths of the sample solution in a rather effortless manner. Longer than 91.2 cm injection is still possible. It is not performed, however, owing to loss of resolution as observed in FIG. 14 (panel e). The electrochromatogram in panel d or e is believed to be the first demonstration in CEC showing sample injections longer than the total capillary length. The volume of sample injected was also greater than 1 $\mu$l. A comparison of the peak heights obtained in panels a and e suggests improvements in peak heights of 1118 times and 1104 times for decanophenone and pyrene, respectively. These values are the highest reported sensitivity improvements for neutral analytes using a simple on-line preconcentration technique in CEC. The strong interaction of the analytes to the porous matrix and the inherent rapid mass transfer characteristics of the porous matrix allowed for the observation of such marked preconcentration effects.

Successful separations have been done with PSG in 250-$\mu$m i.d. capillaries (data not shown). This work opens the possibility of performing semi-preparative separations involving long plug injections. Injection volumes in the $\mu$l range could easily be made.

EXAMPLE 13

FIG. 15 (panels a, b, c, d, e, and f) are representative electrochromatograms showing plots of absorbance versus retention time using an embodiment of the invention. The plug lengths were 0.1 mm (panel a) and 1.8 cm (panels b, c, d, e, and f). Injections were done using pressure wherein the injection length is fixed at 1.8 cm. The sample solutions were the same as the separation solution (panels a and b), 10 mM phosphoric acid in 20% acetonitrile (panel c), 10 mM phosphoric acid in 70% acetonitrile (panel d), 50 mM phosphoric acid in 40% acetonitrile (panel e), 0.05 mM phosphoric acid in 40% acetonitrile (panel f). The separation solution was 10 mM phosphoric acid in 40% acetonitrile. The peptide concentrations were 16.7 $\mu$g/ml each, the applied voltage was 12 kV, and the absorption detection was at 214 nm. The elution order was bradykinin (peak 1), angiotensin II (peak 2), tripeptide I (peak 3), tripeptide II (peak 4), and methionine enkephalin (peak 5).

Although it was expected that the peak shapes would be better under a gradient condition (FIG. 15, panel c) as compared to a nongradient one (FIG. 15, panel b), the resulting peak shapes were better using a higher concentration of acetonitrile in the sample matrix (FIG. 15, panel d). Better peak shapes were observed in FIG. 15 (panel d) resulting from sample stacking. The broadening effect of using a higher concentration of the eluting solvent in the sample solution (reverse gradient effect due to higher concentration of eluting solvent) is not observed because the cationic peptides immediately migrate to the separation buffer once voltage is applied, thus the peptide zones are already in the separation solution before it reaches the porous matrix. Sample stacking is also shown in FIG. 15 (panel f) where the sample is prepared in a matrix having a lower concentration of buffer component and a similar percentage of acetonitrile compared to the separation solution.

Undesirable peak shapes are observed in FIG. 15 (panel c) resulting from destacking. Destacking is the broadening of charged analytes when analytes pass the concentration boundary that separates regions of low and high electric field strengths. The low electric field zone is the high conductivity sample matrix containing more water. Destacking is also shown in FIG. 15 (panel e) where the sample is prepared in a matrix having a higher concentration of buffer component and a similar percentage of acetonitrile compared to the separation solution.

EXAMPLE 14

FIG. 16 (panels a and b) are representative electrochromatograms showing plots of absorbance versus retention time using an embodiment of the invention. The injections were 0.1 mm using 0.5 p.s.i. pressure (panel a) and 15-s at 5 kV (panel b). The sample solutions were 10 mM phosphoric acid in 40% acetonitrile (panel a) and 0.5 $\mu$M phosphoric acid in 40% acetonitrile (panel b). The peptide concentrations were 16.7 $\mu$g/ml each (panel a) and 167 ng/ml each (panel b). The separation voltage was 12 kV. Other conditions are the same as in Example 13.

The analytes in FIG. 16 (panel b) were one hundred times less concentrated than those in FIG. 16 (panel a). Improvements in peak heights for bradykinin (peak 1), angiotensin II (peak 2), tripeptide I (peak 3), tripeptide II (peak 4), and methionine enkephalin (peak 5) were 1040, 820, 810, 950, and 711 times, respectively. For the preconcentration procedure, %RSDs (n=5) of peak heights ranged from 6.2% to 16.2% while %RSDs (n=5) of migration time ranged from 0.7% to 1.5%. Reproducibility of peak heights should be improved with the use of an internal standard.

Field enhanced sample injection was performed by dissolving the sample in a low conductivity matrix (0.5 µM phosphoric acid in 40% acetonitrile), followed by injection using voltage with the negative electrode at the detector end. As the voltage was applied, the low conductivity sample matrix entered the capillary by virtue of electroosmotic flow (EOF) while the cationic peptides entered the column by virtue of both EOF and electrophoretic flow. Only a very small plug of sample matrix was introduced because the low pH of the separation solution markedly decreases the EOF, which prevents the dissociation of silanol groups at the capillary walls. An unretained neutral solute (thiourea) was actually detected after 30 minutes.

The electric field in the sample matrix zone introduced into the column was much higher than the separation zone. This effect caused the high electrophoretic velocity of the cationic peptides entering the capillary. The high analyte electrophoretic velocity caused a large amount of peptides to be introduced, unlike in hydrodynamic injection, the volume of sample loaded limited the amount of sample introduced. The high analyte electrophoretic velocity also caused focusing or preconcentration of peptides at the concentration boundary between the sample matrix and separation solution (sample stacking). Introduction of a water plug before electrokinetic injection, which is suggested to be useful in sample stacking with electrokinetic injection, did not improve the peak heights because of the similar direction of the EOF and analyte electrophoretic velocities. The low conductivity sample matrix that entered the capillary also maintained the enhancement of the electric field at the inlet end of the capillary during injection.

With the conditions in FIG. 16, optimum electrokinetic injection time at 5 kV was found to be 15 s. Longer injections lead to broadening of the peaks. After the injection, the separation voltage was applied with the same polarity as in the injection (negative electrode at the detector side). The analytes moved to the cathode and were subsequently preconcentrated again based on their retention on the PSG column. The method was considered selective for cations because cations were mostly introduced into the capillary. The injected neutrals migrated after the unretained neutral marker and the cations because the EOF was very slow. At the pH used, all the analytes were either positively charged or neutral. Applicability of the technique to other cationic samples is also possible.

EXAMPLE 15

Table 2 lists the types and volumes of reagents used to make different precursor stock solutions where the ratio of the acid catalyst to the precursor, methacryloxypropyltriethoxysilane, was varied or where the precursor was reacted with a co-precursor (to form a mixed phase PSG monolith).

TABLE 2

| Solution | Volume (µL) | | | |
|---|---|---|---|---|
|  | Precursor[1] | BTE[2] | BTO[3] | HCl[4] |
| A | 375 | 0 | 0 | 100 |
| K | 375 | 200 | 0 | 100 |
| J | 575 | 0 | 0 | 100 |
| M | 500 | 0 | 75 | 100 |
| P | 375 | 200 | 0 | 100 |

[1]methacryloxypropyltriethoxysilane
[2]bis(triethoxysilyl)ethane
[3]bis(triethoxysilyl)octane
[4]0.12 M Either changing the concentration of the precursor in the reaction solution or using a co-precursor for the formation of mixed phases modified the chemical nature of the parent PSG monolith. The PSG monoliths, PSG-A and PSG-J, prepared from solutions A and J, respectively, differ only in the volume of precursor used in the reaction with J containing a higher volume of the precursor than A. A higher volume of the precursor in the reaction should result in a denser monolith in the capillary column. The PSG monolith, PSG-K, was prepared with the precursor and bis(triethoxysilyl)ethane as a co-precursor. The PSG monoliths, PSG-M and PSG-P, were prepared with the precursor and different amounts of bis(triethoxysilyl)octane as the co-precursor. The co-precursors hydrolyze and condense with the precursor to form hybrid sols (mixed phases).

For solutions A and J, the appropriate volume of the precursor was added to 100 µL of the acid catalyst (0.12 M HCl), and the resulting solution was stirred for 15 minutes at room temperature (in the dark). For solutions K, M, and P, the appropriate volume of the precursor was added to 100 µL of 0.12 M HCl followed by the addition of the appropriate amount of bis(triethoxysilyl)ethane; the resulting solution was stirred for 15 minutes at room temperature (in the dark). All of these solutions were used within two hours of their preparation.

A similar procedure was followed in making the toluene/precursor stock solutions with the photoinitiator added. The amount of photoinitiator added to the toluene/precursor stock solution was 10 mg photoinitiator for every 100 µL of the toluene/precursor stock solution.

The capillary was prepared and conditioned in the same manner as previously described. PSG capillary column conditioning was the same as before.

The separation factors of the monoliths for two test mixtures of alkyl phenyl ketones (APKS) and polycyclic aromatic hydrocarbons (PAHs) were determined. The separation factor is a measure of the analyte separation capability of a chromatographic system. The separation factor, $\alpha$, is given by $k_2/k_1$, where k is the retention factor for a particular analyte, and $k_2$ and $k_1$ are the k values for adjacent analytes. The retention factor $k=(t_R-t_o)/t_o$ was determined in the usual way, where $t_R$ is the analyte retention time and $t_o$ is the retention time of an unretained marker, for which we used thiourea Table 3 lists the separation factor of each PSG monolith for naphthalene and pyrene.

TABLE 3

| Monolith | $k_N$ | $k_{Py}$ | $\alpha_{Npy}$ | $R_s(N/Py)$ |
|---|---|---|---|---|
| PSG-A | 0.14 | 0.36 | 2.57 | 2.43 |
| PSG-K | 0.23 | 0.56 | 2.43 | 4.09 |
| PSG-J | 0.31 | 0.79 | 2.55 | 4.35 |

TABLE 3-continued

| Monolith | $k_N$ | $k_{Py}$ | $\alpha_{Npy}$ | $R_6(N/Py)$ |
|---|---|---|---|---|
| PSG-M | 0.35 | 0.90 | 2.57 | 4.37 |
| PSG-P | 0.25 | 0.69 | 2.76 | 9.03 |

The values for α varied from 2.43 for PSG-K to 2.76 for PSG-P with the separation factor for PSG-P being slightly higher than that of the other monoliths. Separation factors greater than 1 indicated successful separation of the analytes.

FIG. 17 (panels a, b, c, d, and e) are representative electrochromatograms showing plots of absorbance versus retention time using an embodiment of the invention. A mixture of thiourea (T), naphthalene (N), phenanthrene (Ph), and pyrene (Py) were separated on PSG-A (FIG. 17, panel a), PSG-K (FIG. 17, panel b), PSG-J (FIG. 17, panel c), PSG-M (FIG. 17, panel d), and PSG-P (FIG. 17, panel e). In all cases the peaks of the different analytes were well resolved.

Resolution was determined from the expression $$R_s = \frac{\sqrt{N}}{4} \frac{(\alpha-1)}{\alpha} \frac{k}{(k+1)},$$

where N is the efficiency (theoretical plate number), α is the separation factor, and k the retention factor for a particular analyte. PSG-A has the lowest resolution of 2.43 for naphthalene and pyrene whereas PSG-J has a resolution of 4.35 for the same two analytes. The higher volume of the precursor used in the preparation of PSG-J as compared to PSG-A resulted in increased hydrophobicity of the monolith The retention factors for naphthalene and pyrene on PSG-J were 0.31 and 0.79, respectively, and these values reflected the increase in the hydrophobicity of the monolith. These values represent increases of 55% and 54%, respectively.

The use of the co-precursor, bis(triethoxysilyl)octane in PSG-M and bis(triethoxysilyl)ethane in PSG-K and PSG-P resulted in resolution for naphthalene and pyrene of 4.37, 4.09, and 9.03, respectively, which is an enhancement of up to 73% as compared to the resolution on the parent PSG-A (Rs=2.43). The retention factors for naphthalene (0.23) and pyrene (0.56) were both 60% higher for these three monoliths than for PSG-A.

EXAMPLE 16

The separation column was prepared as described above in Example 15 for monolith PSG-J. For a porous matrix having a length of 15 cm, the retention factors for napthalene and pyrene, $k_N$ and $k_{Py}$, respectively, were 0.31 and 0.79, respectively, for a porous matrix made with 80% toluene. For a similar porous matrix having a length of 10 cm, $k_N$ and $k_{Py}$ were 0.10 and 0.24, respectively. There was a linear relationship between length and $k_N$ (r=0.991) and $k_{Py}$ (r=0.991). The separation factors for 15-cm, 10-cm, and 5-cm porous matrices were 2.55, 2.52, and 2.40, respectively. Thus, for the shortest monolith length, a high separation factor was maintained, while the elution times for the analytes were significantly reduced. Decreasing the length of the porous matrix in a capillary column led to a decrease in the elution times of the test analytes. Decreasing this length had an effect of decreasing the retention factors of naphthalene and pyrene.

EXAMPLE 17

The separation column was prepared as described above in Example 15. For PSG-A made with 80% toluene, $k_N$ was 0.14 and $k_{Py}$ is 0.36, whereas $k_N$ was 0.30 and $k_{Py}$ was 0.74 for PSG-A made with 73% toluene. The separation factors for PSG-A made with 80% toluene and 73% toluene were 2.57 (0.1%RSD) and 2.47 (0.1%RSD), respectively. The value of k increased by 53% and 51% for naphthalene and pyrene when 73% toluene was used in the preparation of the monoliths.

A similar trend was observed for PSG-J where $k_N$ was 0.31 and $k_{Py}$ was 0.79 for a monolith made with 80% toluene. The $k_N$ (0.49) and $k_{Py}$ (1.23) values increased by 37% and 36% when the concentration of toluene was decreased from 80% to 73%. The separation factors of PSG-J made with 80% toluene and 73% toluene were 2.55 and 2.51, respectively.

The resolution of naphthalene and pyrene differed significantly when comparing PSG monoliths made with 80% and 73% toluene. When the pore size decreased, which was brought about by using lower volumes of toluene, the PSG surface increased with a resulting increase in the retention and resolution under the same separation solution conditions. Thus, the permeability of the porous matrix affects the retention of the analytes.

EXAMPLE 18

Materials. The 5 μm spherical chiral particles modified with (S)-N-3,5-dinitrobenzoyl-1-naphthylglycine were provided by the Graduate School of Pharmaceutical Sciences, University of Tokyo (Tokyo, Japan) and Sumika Chemical Analysis Service (Osaka, Japan). D- and L-amino acids, D- and L-non-protein amino acids (NPAAs), 3-(trimethoxysilyl)propyl methacrylate and 4-fluoro-7-nitro-2,1,3-benzoxadiazole (NBD-F) were purchased from Sigma (St Louis, Mo., USA) or Aldrich (Milwaukee, Wis., USA) or Fluka (Ronkonkoma, N.Y., USA) and were used as received. Irgacure 1800 was from Ciba (Tarrytown, N.Y., USA). Doubly distilled water was used in the preparation of all samples and buffers. HPLC-grade acetonitrile was purchased from Aldrich and used without further purification.

Frit Fabrication and Column Packing. The photopolymerization procedure was carried out as described in M. Kato, M. Dulay, B. Bennett, J. Quirino, and R. Zare, *Journal of Chromatography A*, 924 (2001), pp. 187–195. In situ free-radical polymerization was initiated by irradiating the monomer solution in fused-silica capillaries (75 μm i.d.×365 μm o.d.) that were purchased from Polymicro Technologies (Phoenix, Ariz., USA). Irradiation of the monomer solutions was carried out by an XL-1500 UV crosslinker (Spectronics, Westbury, N.Y., USA) which has six 15 W fluorescent blacklight tubes, producing UV light of predominantly 365 nm wavelength.

The sol-gel solution was made up of 750 μl of 3-(trimethoxysilyl)propyl methacrylate, 22.5 μl of 0.12 M hydrochloric acid and 225 μl of water, and was stirred for 30 minutes in the dark at room temperature. A 170 μl volume of toluene was added to 30 μl of the sol-gel solution and stirred for 30 minutes at room temperature. An 8.9 mg amount of Irgacure 1800 was added to the toluene mixture and stirred for 1 hour at room temperature. This procedure forms what we refer to as solution A.

The outlet frit was prepared first. About a 3 mm section of the polyimide coating about 10 cm from the end of a 30-cm long capillary was removed with a razor. The capillary was then filled with solution A using a syringe. Before the capillary was exposed to UV light for 5 minutes, both ends of the capillary were sealed with parafilm. The presence of a frit was confirmed by inspection at 100× magnification. The monolithic material has an opaque appearance and is very porous.

The capillary was rinsed with ethanol by pressure from a syringe to remove the unreacted solution. A 15 cm packed chiral section was prepared in the capillary by introducing a sonicated (for 5 minutes) slurry of 10 mg of chiral particles into the capillary column with a syringe and a hand-held vise.

Lastly, the inlet frit was prepared in the column in the same manner as the outlet frit. A 3 mm section of the polyimide coating about 25 cm from the outlet of the capillary and 15 cm from the outlet frit was removed. Solution A was introduced into the capillary with a syringe pressurized with a hand-held vise. The resulting frit is located immediately at the end of the packed section.

A detection window was created immediately after the packed section at the outlet by using hot sulfuric acid (>100° C.). The column was preconditioned with running buffer that had been degassed by sonication (by pressurizing the column inlet to approximately 200 p.s.i. with a hand-held vise). Next, the column was further conditioned in the CE instrument by electrokinetically driving the buffer mobile phase through the capillary at an applied voltage of 15 kV until a stable baseline was achieved. This procedure typically takes 2 to 3 hours to complete.

Derivatization of amino acids. A 10 μl volume of each 5 mM amino acid or NPAA in 0.2 M borate buffer (pH 8.0) and 10 μl of 5 mM NBD-F in acetonitrile were mixed and heated at 60° C. for 5 minutes. After addition of 20 μl of running buffer, the mixture was electrokinetically injected into the capillary at 10 kV for 5 seconds.

Separation. All separations were performed on a Beckman P/ACE 5000 capillary electrophoresis system (Fullerton, Calif., USA). The instrument was equipped with an air-cooled 488 nm argon ion laser. A capillary column with a 15 cm chiral packed section was used for the separation of amino acids. The derivatized amino acid sample was injected into the column electrokinetically (0.33 kV/cm) at a temperature of 20° C. Applied voltages during the separations are mainly 0.83 kV/cm or 0.50 kV/cm. The elution time of an unretained compound is taken to be the time from injection to the occurrence of the first solvent disturbance peak. The velocity of the first disturbance peak is 1.28 mm/s, when 0.83 kV/cm is applied through the column. The analytes were observed by monitoring their fluorescence intensities (excitation wavelength is 488 nm with a band pass filter of 520 nm for emission). The efficiency of an enantiomeric separation is measured by the value of the resolution factor, which is defined as:

Resolution=$2(t_A-t_B)/(W_A+W_B)$ where $t_A$ is the retention time of a more retained enantiomer (A), $t_B$ is the retention time of a less retained enantiomer (B), and $W_A$ and $W_B$ are peak widths of species A and B.

Scanning electron microscopy (SEM) analysis. A packed capillary was sectioned into 5-mm segments. These segments were sputtered with gold for SEM analyses. SEM analyses were performed on a scanning electron microscope (Philips SEM 505, Eindhoven, The Netherlands).

The packed capillaries used in the experiments described here in Example 18 can be thought of as having three sections: (1) the outlet frit, (2) the packed section, and (3) the inlet frit. As seen in FIG. 18, the outlet frit appears to be made of a network of interconnecting 1 μm diameter spherical structures. There are no particles embedded within the outlet frit. There are 3 μm channels (dark areas) seen throughout the sol-gel network. These channels allow passage of ions and liquid, but prevent the escape of chiral particles.

As shown in FIG. 19, however, the inlet frit does contain some embedded chiral particles. This is a result of the particles mixing with solution A as it entered the packed section of the capillary prior to irradiation. The interconnecting spherical structures that comprise the outlet frit are no longer apparent. Instead, the SEM micrograph (FIG. 19) shows some amorphous structure that covers and binds the chiral particles to form the inlet frit. The structural differences observed between the two frits in the presence and absence of particles is similar to that reported by others.

FIG. 20 is a micrograph of a section of the packed segment of the capillary. The sol-gel material did not form in any part of the packed segment because the polyimide coating blocked the UV light from entering this section of the capillary during the photopolymerization of the frits. Therefore, the packed segment is only made up of chiral particles that are held in place by the outlet and inlet frits.

Chiral separation. The performance of the packed chiral columns was studied by separating fluorescently derivatized amino acids. The results were then compared to previously reported amino acid separations done on monolithic columns using a sol-gel material to embed the same chiral particles. In previous reports, mixtures of 13 derivatized amino acids and three NPAAs were separated on a chiral particle-loaded monolithic column using a separation solution of 5 mM phosphate buffer (pH 2.5) and acetonitrile. The same mixtures of amino acids and NPAAs were separated using the packed columns under the same conditions as previously. Specifically, the separation solution is a mixture of 5 mM phosphate buffer (pH 2.5)-acetonitrile (30:70), the field strength is 0.50 kV/cm, and the temperature is 20° C.

Table 4 lists the retention times, resolutions, elution orders, and plate heights of NBD-amino acids and NBD-NPAAs.

TABLE 4

Elution time, resolution, and plate height for NBD-amino acid enantiomer separations

| | Elution time for first eluted enantiomer (min) | Elution time for second eluted enantiomer (min) | Resolution | Elution order | Plate height for first eluted enantiomer (μm) |
|---|---|---|---|---|---|
| Alanine | 8.28 | 8.35 | 4.01 | n, L | 8.7 |
| Glutamine | 7.23 | 7.97 | 2.63 | n, L | 14 |
| Glutamic acid | 39.72 | 42.20 | 1.31 | n, L | 20 |
| Glycine | 8.43 | | | | 16 |
| Isoleucine | 6.92 | 8.10 | 4.41 | n, L | 12 |
| Methionine | 7.24 | 8.61 | 4.90 | n, L | 12 |
| Phenyl-alanine | 7.76 | 9.14 | 4.68 | n, L | 12 |
| Proline | 11.06 | 11.65 | 1.38 | L, n | 13 |
| Serine | 7.49 | 8.29 | 3.02 | n, L | 11 |
| Threonine | 6.24 | 6.91 | 2.77 | n, L | 13 |
| Valine | 7.40 | 8.54 | 5.03 | n, L | 11 |
| 2,3-Di-aminopropionic acid | 7.17 | 8.35 | 8.29 | NI | 39 |
| 2-Amino-butyric acid | 7.17 | 8.35 | 3.78 | NI | 13 |
| 3-Amino-butyric acid | 6.3 | 6.84 | 1.89 | NI | 18 |

N.I.: Not identified.

Most of NBD-amino acids and NBD-NPAAs are eluted within 10 minutes, whereas NBD-glutamic acid (Glu) enantiomers are eluted in 40 minutes. In a packed column, the retention times of the amino acids are shortened as compared to the same separation in a particle-loaded monolithic column. Under our experimental conditions, the electroosmotic flow is very small or negligible and electrophoretic velocity is the main driving force for analyte migration through the column. The separation solution and applied voltage of the packed column and the monolithic column are the same, so electrophoretic velocity of these analytes are similar between the packed column and the monolithic column. The different retention times between the two columns are derived from the different partitioning between the mobile and the stationary phases. Structural differences between the packed and the monolithic columns contribute to the differences observed in the partitioning of the analytes.

Using the chiral column made with the photopolymerized sol-gel frits, all the NBD-amino acids and NBD-NPAAs were well resolved. The resolution factors are between 1.21 and 8.29. These values are about 1.5 times larger than those in the particle-loaded monolithic columns. The elution orders of the NBD-amino acids on the packed columns are the same as those on the monolithic columns, with the NBD-D-amino acids eluting faster than the corresponding NBD-L-amino acids, except for NBD-Pro. The elution orders of NBD-NPAAs were not confirmed, because the samples were made up of racemic mixtures rather than optically active ones.

The plate heights for NBD-amino acids and NBD-NPAAs were less than 20 $\mu$m on the packed column, except for NDD-Glu and NBD-2,3-diaminopropionic acid. In the monolithic columns, the plate heights for NBD-amino acids and NBD-NPAAs are between 14 and 65 $\mu$m. These plate heights are about two times larger than those in the packed column.

These NBD-Glu and NBD-2,3-diaminopropionic acid showed worse separations than other NBD-amino acids and NBD-NPAAs in both the packed and monolithic columns. In chromatographic separations, additional interactions that lead to reductions in the velocity of mass transfer increase the plate height of an analyte. Glu has two carboxyl groups that form ionic interactions with the unmodified amino groups of the aminopropyl silica gel. Two amino groups of 2,3-diaminopropionic acid are derivatized with NBD structures, making it different from the other amino acids and NPAAs. These two NBD structures might form some additional $\pi$-$\pi$ interactions with the packing particle. Therefore NBD-Glu and NBD-2,3-diaminopropionic acid showed worse separations than the others did in both packed and monolithic columns. The plate heights for all NBD derivatives, including NBD-Glu and NBD-2,3-diaminopropionic acid, are smaller for the packed column than the monolithic column.

FIG. 21A shows the electrochromatogram of a sample of NBD-DL-alanine (Ala) and NBD-DL-threonine (Thr) on the packed column, while FIG. 21B is the electrochromatogram of the same sample on the monolithic column. Similar elution times were achieved on the packed column as compared to the monolithic column by using an applied electric field of 0.5 kV/cm. A peak observed at about 6 minutes in FIG. 21B arises from the hydrolysis of the fluorogenic reagent. The separation between the amino acids is vastly improved on the packed column. As seen in FIG. 21, baseline separations of the sample components were achieved with the packed column as compared to the monolithic column. The peak shape of each NBD-amino acid in the packed column is much sharper than in the monolithic column. These results show that the separation efficiency of the packed column is superior to that of the monolithic column.

The improvement in the separation efficiency and resolution of the sample of amino acids in the packed column as compared to the monolithic column may arise from better interaction of the amino acids with the chiral particles. In the particle-loaded, monolithic columns, the particles may have been partially shielded as a result of encapsulation of the particles in the sol-gel matrix. In the absence of the sol-gel matrix, mass transfer is improved. Another reason for lower separation efficiency on the monolithic column might come from some heterogeneity in the sol-gel structure, such as small gaps or cracks. Such gaps or cracks occur as ethanol is evaporated from the reaction mixture during the thermal polymerization of the sol-gel used to embed chiral particles. Photopolymerization allows us to avoid using heat, and consequently to avoid the formation of these gaps or cracks within the monolithic structure.

An additional advantage to using photopolymerized sol-gel to form frits is the ease and speed in preparation and the ease in controlling the length and the position of the frits as compared to the preparation of other photopolymerized or silicate frits. A frit is made in 5 minutes upon exposure to UV light in our packed columns. The use of methacrylate-based reagents for frits required 1–16 hours of polymerization time. In case of silicate frits, only a few seconds are required for fabrication, but pretreatment of the capillary wall is required. Consequently, preparation of packed capillaries using silicate frits requires an hour to fabricate the packed columns. Furthermore, it is more difficult to control the position and placement of flits that are prepared by heating.

Owing to the high porosity of the sol-gel frit, only 30 minutes at very low pressure (about 200 p.s.i. from a syringe on a hand-held vise) is required to pack a 15 cm section of chiral particles in the capillary. The backpressure is very low with the photopolymerized sol-gel frits as compared to silicate or photopolymerized methacrylate frits.

Performance of short-packed segment columns. In the packed column, the plate heights of the NBD-amino acid enantiomers are two-times smaller than the monolithic column. Consequently, NBD-amino acids are expected to be separated by a short packed column with a short separation time. Separation of NBD-amino acid enantiomers (NBD-Phe, -Val, -Gln, -Thr) are separated on a 5 cm packed segment column. The short packed column separates NBD-Phe enantiomers within only 5 minutes. (FIG. 22). The separation factor for NBD-Phe enantiomers and the plate height for NBD-D-Phe are 2.22 and 8 $\mu$m, respectively. The plate height is improved on the short packed column, however the separation factor is decreased owing to the short packing segment.

EXAMPLE 19

Preparation of the PSG monolith. The preparation of the parent PSG structure in a capillary column has previously been described. The procedure used to derivatize the surface of the parent PSG with a bonded phase has also been described. However, the length of the derivatization reaction usually takes twice as long in the larger i.d. capillary as compared to the small i.d. capillary.

Separation. A mixture of thiourea, acetophenone, propiophenone, and butyrophenone (all in millimolar quantities) have been electrokinetically injected into a PSG-filled capillary. The minimum injection time is 15 s. The applied voltage ranges from 8 kV to 15 kV.

A UV-absorbance detector is used to detect the analyte peaks. A high-voltage power supply is used to apply voltage to the capillary. All other experimental details are similar to that already published on the analytical (small i.d.) PSG-filled capillaries. Stock solutions of each of the analytes were prepared as 1 mg of the alkyl phenyl ketone in 1 mL of acetonitrile. A 50 mM stock solution of thiourea in water was used in the preparation of the sample solutions.

Results. The separation of the analytes follows the same reversed-phase mechanism where the more hydrophobic analytes elute later than the less hydrophobic ones. Preconcentration of the analytes is observed as the injection time (i.e., plug length) is increased.

In FIG. 23, a mixture of thiourea and alkyl phenyl ketones were preconcentrated and separated on a 250 μm i.d. capillary filled with a 10 cm PSG monolith derivatized with a $C_8$ bonded phase (PSG-$C_8$). Long injection plug lengths allowed for the loading of up to 0.74 ng of propiophenone onto the column. The peaks become sharper with the higher loading. It is believed that more analytes can be loaded onto the column before there is a compromise in peak shape and height and preconcentration can no longer is achieved.

The amount of propiophenone loaded onto the column can be increased to 7.43 ng by using a 350 μm i.d. capillary filled with the same PSG monolith as demonstrated in FIG. 24. There is little loss in resolution but the peaks have broadened.

FIG. 25 shows the separation of thiourea and propiophenone in a 540 μm i.d. capillary filled with the same PSG monolith. 0.86 ng of propiophenone was loaded onto the column with a short injection length of 3.73 mm.

An easy and fast method for the preparation of packed columns using photopolymerized sol-gel frits and monoliths has been developed. Bubble formation is not observed during any of the chromatographic runs. While the invention has been described above by reference to various embodiments, it will be understood that changes and modifications can be made without departing from the scope of the invention. The invention includes all that fits within the literal and equitable scope of the appended claims. All references referred to above are incorporated herein by reference in their entireties.

What is claimed is:

1. A separation column comprising:
   a separation channel; and
   a porous matrix in the channel, said porous matrix comprising a metal organic photopolymer from a metal alkoxide precursor, wherein the porous matrix is homogeneous and contains no chromatographic particles.

2. The column of claim 1, wherein said porous matrix comprises a separation medium.

3. The column o f claim 2, wherein the separation channel has a channel wall, and the medium is attached to the channel wall and fills at least a section of the channel.

4. The column of claim 2, wherein the porous matrix has an affinity for an analyte.

5. The column of claim 1, wherein the metal alkoxide comprises a metal or a metalloid selected from the group consisting of aluminum, barium, antimony, calcium, chromium, copper, erbium, germanium, iron, lead, lithium, phosphorus, potassium, silicon, tantalum, tin, titanium, vanadium, zinc, and zirconium.

6. The column of claim 1, wherein the metal alkoxide comprises at least one photoactive group.

7. The column of claim 1, wherein the separation channel is a capillary separation channel or a planar structure.

8. The column of claim 1, wherein said porous matrix comprises at least one frit adapted to retain a separation medium in the channel.

9. The column of claim 8, wherein the at least one frit has a controlled porosity.

10. The column of claim 8, wherein the frit is bound to an inner surface of the channel wall.

11. The column of claim 8, wherein the separation channel extends between an inlet and an outlet and has a channel wall, and wherein the at least one frit is adjacent to at least one of the inlet and the outlet.

12. The column of claim 8, wherein the separation channel is a fused-silica capillary having an internal dimension in the range of between about 5 and 1000 μm, and the frit is of a structure sufficient to withstand high pressure during packing of the separation medium in the channel.

13. The column of claim 1, further comprising at least one frit produced from a methacrylate-substituted silicate.

14. The column of claim 13, the methacrylate-substituted silicate is photocurable.

15. The column of claim 1, said column having a first portion that is filled with a separation medium and a second portion adjacent to said first portion that transmits radiation.

16. The column of claim 15, wherein said second portion does not contain said separation medium.

17. A separation column comprising:
   a separation channel; and
   a porous matrix in the channel, said porous matrix comprising a metal organic photopolymer from a metal alkoxide precursor.

* * * * *

UNITED STATES PATENT AND TRADEMARK OFFICE
CERTIFICATE OF CORRECTION

PATENT NO. : 6,875,348 B2
APPLICATION NO. : 10/124654
DATED : April 5, 2005
INVENTOR(S) : Richard N. Zare et al.

It is certified that error appears in the above-identified patent and that said Letters Patent is hereby corrected as shown below:

Column 6, line 3, please insert:

--In accordance with embodiments of the invention, porous matrix 15 can be utilized in a number of varying applications. In one embodiment, shown in Fig. 1B, porous matrix 15 can be used as a separation medium 20 designed to preconcentrate and/or separate analytes. In this embodiment, porous matrix 15 tends to comprise a relatively longer and continuous structure that is generally homogenous. As used herein, the term monolith refers to the relatively longer and continuous porous matrix 15 that functions as a separation medium.--

Column 6, line 65, please delete "methacryloxy-propyltrimetoxy silane" and insert --methacryloxypropyltrimethoxysilane--.

Column 7, line 7, please delete "apore-size" and insert --a pore-size--.

Column 7, line 20, please delete "(1)" and insert --(1).--.

Column 7, line 27, please delete "(2)" and insert --(2),--.

Column 8, line 59, please delete "methacryloxypropyltrimethoxy silane" and insert --methacryloxypropyltrimethoxysilane--.

Column 8, line 65, please delete "antacid" and insert --an acid--.

Column 12, line 65, please delete "semipreparative, applications." and insert --semipreparative applications.--

Column 13, line 23, please delete "alkyl benzene ketones" and insert --alkyl benzenes,--

Column 14, line 49, please delete "20° C." and insert --20° C--.

Column 14, line 60, please delete "20° C." and insert --20° C--.

Column 14, line 63, please delete "hexylbenzene." and insert --hexyl benzene.--.

Column 15, line 17, please delete "20° C." and insert --20° C--.

Column 16, line 59, please delete "34.2 nm." and insert --34.2 mm.--.

Column 22, line 11, please delete "(panel c)," and insert --(panel e),--.

UNITED STATES PATENT AND TRADEMARK OFFICE
CERTIFICATE OF CORRECTION

| | | |
|---|---|---|
| PATENT NO. | : 6,875,348 B2 | |
| APPLICATION NO. | : 10/124654 | |
| DATED | : April 5, 2005 | |
| INVENTOR(S) | : Richard N. Zare et al. | |

It is certified that error appears in the above-identified patent and that said Letters Patent is hereby corrected as shown below:

Column 24, line 55, please delete "$k=(t_R-t_0)/t_0$" and insert --$k(t_R-t_0)/t_0$--.

Column 24, line 58, please delete "thiourea" and insert --thiourea.--.

Column 24, line 62, please delete "$R_6(N/Py)$" and insert --$R_S(N/Py)$--.

Column 25, line 33, please delete "monolith" and insert --monolith.--

Column 25, line 43, please delete "(Rs=2.43)" and insert --($R_s$=2.43)--.

Column 25, line 50, please delete "$k_N$ and $k_{Py}$," and insert --$k_N$ and $k_{Py}$,--.

Column 25, line 52, please delete "$k_N$" and insert --$k_N$--.

Column 25, line 53, please delete "$k_{Py}$" and insert --$k_{Py}$--.

Column 25, line 54, please delete "$k_N$" and insert --$k_N$--.

Column 25, line 54, please delete "$k_{Py}$" and insert --$k_{Py}$--.

Column 25, line 67, please delete "$k_N$" and insert --$k_N$--.

Column 26, line 1, please delete "$k_{Py}$" and insert --$k_{Py}$--.

Column 26, line 8, please delete "$k_N$" and insert --$k_N$--.

Column 26, line 9, please delete "$k_{Py}$" and insert --$k_{Py}$--.

Column 26, line 10, please delete "$k_N$" and insert --$k_N$--.

Column 26, line 10, please delete "$k_{Py}$" and insert --$k_{Py}$--.

Column 27, line 18, please delete "C.)" and insert --C)--.

Column 27, line 29, please delete "60° C." and insert --60° C--.

Column 28, line 49, please delete "1.31" and insert --1.21--.

UNITED STATES PATENT AND TRADEMARK OFFICE
CERTIFICATE OF CORRECTION

| | | |
|---|---|---|
| PATENT NO. | : 6,875,348 B2 | Page 3 of 3 |
| APPLICATION NO. | : 10/124654 | |
| DATED | : April 5, 2005 | |
| INVENTOR(S) | : Richard N. Zare et al. | |

It is certified that error appears in the above-identified patent and that said Letters Patent is hereby corrected as shown below:

Column 28, line 53, please delete "8.61" and insert --8.63--.

Signed and Sealed this

Nineteenth Day of December, 2006

JON W. DUDAS
*Director of the United States Patent and Trademark Office*